United States Patent
Merli et al.

(10) Patent No.: US 7,442,806 B2
(45) Date of Patent: Oct. 28, 2008

(54) PROCESSES FOR PREPARING DARIFENACIN HYDROBROMIDE

(75) Inventors: Valeriano Merli, Cremella Lecco (IT); Augusto Canavesi, Locate Varesino (IT); Paola Daverio, Milan (IT)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 11/647,109

(22) Filed: Dec. 27, 2006

(65) Prior Publication Data

US 2007/0197631 A1   Aug. 23, 2007

Related U.S. Application Data

(60) Provisional application No. 60/873,680, filed on Dec. 7, 2006, provisional application No. 60/859,332, filed on Nov. 15, 2006, provisional application No. 60/850,184, filed on Oct. 5, 2006, provisional application No. 60/837,407, filed on Aug. 10, 2006, provisional application No. 60/836,557, filed on Aug. 8, 2006, provisional application No. 60/812,579, filed on Jun. 8, 2006, provisional application No. 60/809,147, filed on May 25, 2006, provisional application No. 60/776,311, filed on Feb. 23, 2006, provisional application No. 60/772,250, filed on Feb. 9, 2006, provisional application No. 60/754,395, filed on Dec. 27, 2005.

(51) Int. Cl.
*C07D 405/00*   (2006.01)

(52) U.S. Cl. .................................................. 548/525

(58) Field of Classification Search .......... None
See application file for complete search history.

(56) References Cited

U.S. PATENT DOCUMENTS

| 5,096,890 A | 3/1992 | Cross et al. |
| 5,233,053 A | 8/1993 | Cross et al. |
| 6,333,198 B1 | 12/2001 | Edmeades et al. |
| 2003/0191176 A1 | 10/2003 | Dunn et al. |
| 2004/0138289 A1 | 7/2004 | Richards et al. |
| 2004/0220224 A1 | 11/2004 | Richards et al. |

FOREIGN PATENT DOCUMENTS

| CA | 2 480 287 | 10/2003 |
| EP | 0 388 054 | 9/1990 |
| JP | 2282360 | 11/1990 |
| JP | 7149640 | 6/1995 |
| WO | WO 03/080599 | 10/2003 |
| WO | WO 2004/039798 | 5/2004 |
| WO | WO 2004/091597 | 10/2004 |

OTHER PUBLICATIONS

ICH Good Manufacturing Practice Guide for Active Pharmaceutical Ingredients, Q7A, Current Step 4 Version (Nov. 10, 2000).
Strobel, H.A. et al, Chemical Instrumentation: A Systematic Approach, 3d ed., pp. 391-393, 894, 922, 924, 925, 953, Wiley & Sons, New York (1989).
Snyder, L.R. et al, Introduction to Modern Liquid Chromatography, pp. 549, 552, 571-572, 2d ed., John Wiley & Sons, New York (1979).
Tomori, H. et al, "Lipase-Catalyzed Practical Synthesis of (R)-1-Benzyl-3-Hydroxy-2, 5-Pyrrolidinedione and Its Related Compunds", *Bulletin of the Chemical Society of Japan*, vol. 69, No. 1, pp. 207-215, (1996).
Graul et al., "Darifenacin", *Drugs of the Future*, 21(11): 1105-1108 (1996).
Hashimoto et al., "A Novel Decarboxylation of α-Amino Acids. A Facile Method of Decarboxylation by the Use of 2-Cyclohexen-1-One as a Catalyst", *Chemistry Letters*, 6: 893-896.

*Primary Examiner*—Kamal Saeed
*Assistant Examiner*—Sun Jae Y Loewe
(74) *Attorney, Agent, or Firm*—Kenyon & Kenyon LLP

(57) ABSTRACT

The invention encompasses processes for the preparation of darifenacin hydrobromide.

1 Claim, No Drawings

PROCESSES FOR PREPARING DARIFENACIN HYDROBROMIDE

CROSS-REFERENCE TO RELATED APPLICATIONS

This application claims the benefit of priority to U.S. provisional application Ser. Nos. 60/754,395, filed Dec. 27, 2005; 60/772,250, filed Feb. 9, 2006; 60/776,311, filed Feb. 23, 2006; 60/809,147, filed May 25, 2006; 60/812,579, filed Jun. 8, 2006; 60/836,557, filed Aug. 8, 2006; 60/837,407, filed Aug. 10, 2006; 60/850,184, filed Oct. 5, 2006; 60/859,332, filed Nov. 15, 2006; and 60/873,680, filed Dec. 7, 2006, hereby incorporated by reference. This application is also related to U.S. application Ser. Nos. 11/646,919, filed Dec. 27, 2006, and entitled "Processes for Preparing Darifenacin Hydrobromide" and 11/646,915, filed Dec. 27, 2006, and entitled "Pure Darifenacin Hydrobromide Substantially Free of Oxidized Darifenacin and Salts Thereof and Process for the Preparation Thereof", hereby incorporated by reference.

FIELD OF THE INVENTION

The invention encompasses processes for the preparation of darifenacin hydrobromide.

BACKGROUND OF THE INVENTION

Darifenacin, (S)-2-{1-[2-(2,3-dihydrobenzofuran-5-yl) ethyl]-3-pyrrolidinyl}-2,2-diphenylacetamide, a compound having the chemical structure,

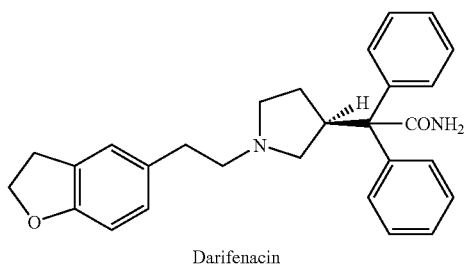

Darifenacin is a selective M3 receptor antagonist. Blockade of destructor muscle activity manifests in an increase in urine volume that the bladder can retain, reduction of urination frequency, and decrease in pressure and urgency associated with the urge to urinate, and thereby episodes of incontinence are reduced.

Darifenacin is administered as the hydrobromide salt, (S)-2-{1-[2-(2,3-dihydrobenzofuran-5-yl)ethyl]-3-pyrrolidinyl}-2,2-diphenylacetamide hydrobromide, of the structure

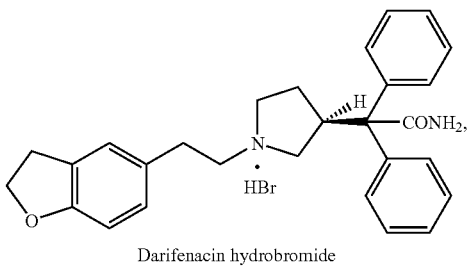

Darifenacin hydrobromide and is marketed under the trade name ENABLEX® by Novartis.

U.S. Pat. No. 5,096,890, hereby incorporated by reference, discloses three routes for the synthesis of darifenacin hydrobromide; all of which comprise the cumbersome and hazardous Mitsunobu reaction, described in the following Scheme.

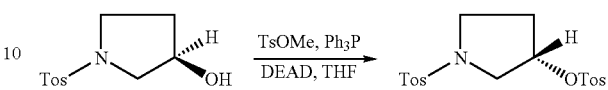

Accordingly, 1-tosyl-3-(R)-pyrrolidinol is reacted with methyl tosylate, and with diethylazodicarboxylate (DEAD), a very dangerous reagent. Typically, the product is contaminated with triphenylphosphine oxide, which is very difficult to separate from the desired product. Moreover, other toxic and hazardous reagents, such as pyridine and NaH, are used in other steps of the synthesis.

The process disclosed in U.S. publication No. 20003/0191176 for the preparation of darifenacin hydrobromide requires the use of $BF_3$, which is a toxic reagent.

Therefore, there is a need in the art for a process for the preparation of darifenacin hydrobromide that does not use toxic and dangerous reagents and that can be performed on an industrial scale. The present invention provides such processes.

SUMMARY OF THE INVENTION

The invention encompasses a process for preparing darifenacin hydrobromide. The process comprises: a) combining 3-(S)-(+)-hydroxypyrrolidine, a solvent selected from the group consisting of a $C_{6-9}$ aromatic hydrocarbon, a polar aprotic organic solvent, and mixtures thereof, a sulfonyl halide, and a base to obtain 1-X-sulfonyl-3-(S)-(−)-X-sulfonyloxypyrrolidine of formula I,

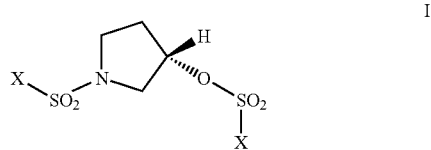

I b) reacting the 1-X-sulfonyl-3-(S)-(−)-X-sulfonyloxypyrrolidine of formula I, diphenylacetonitrile, and an inorganic base, in an organic solvent selected from the group consisting of a $C_{6-9}$ aromatic hydrocarbon, a polar aprotic organic solvent, and mixtures thereof, to obtain (S)-2,2-diphenyl-2-(1-X-sulfonyl-3-pyrrolidinil)acetonitrile of formula II;

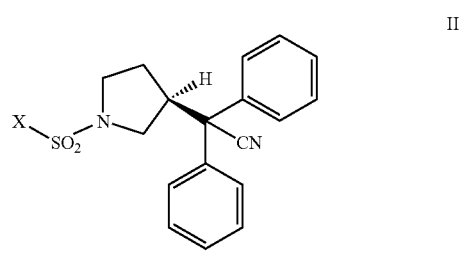

II c) reacting the (S)-2,2-diphenyl-2-(1-X-sulfonyl-3-pyrrolidinil) acetonitrile intermediate of formula II, a bromine acceptor selected from the group consisting of phenol and naphthol, and an acid to obtain (S)-2,2-diphenyl-2-(3-pyrrolidinil) acetonitrile salt of formula III,

III

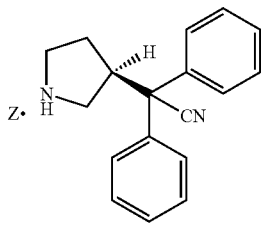

wherein the bromine acceptor is phenol only when the acid is HBr;

d) combining the (S)-2,2-diphenyl-2-(3-pyrrolidinil)acetonitrile salt of formula III, a compound of the formula V,

V

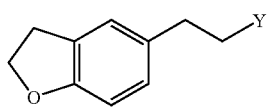

a solvent selected from the group consisting of a $C_{6-9}$ aromatic hydrocarbon, a polar organic solvent, water, and mixtures thereof, and a base to obtain a mixture;

e) heating the mixture of step d;

f) admixing the mixture of step d with an acid to obtain a (S)-2-{1-[2-(2,3-dihydrobenzofuran-5-yl)ethyl]-3-pyrrolidinyl}-2,2-acetonitrile salt of formula IV; and

IV

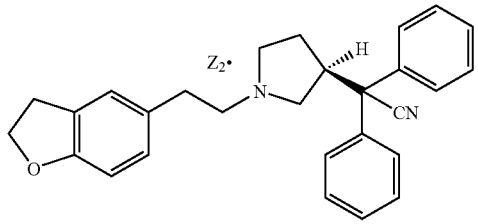

g) admixing the (S)-2-{1-[2-(2,3-dihydrobenzofuran-5-yl)ethyl]-3-pyrrolidinyl}-2,2-acetonitrile salt of formula IV, an inorganic base and a protic solvent; and h) reacting with hydrobromic acid to obtain darifenacin hydrobromide, wherein X is either $C_{1-10}$ alkyl or $C_{6-9}$ aryl, wherein Y is a leaving group selected from the group consisting of I, Cl, Br, mesyl, tosyl, brosyl, trifluoroacetyl, and trifluoromethansulfonyl, wherein $Z_1$ and $Z_2$ are independently an acid.

The invention also encompasses a process for preparing a (S)-2-{1-[2-(2,3-dihydrobenzofuran-5-yl)ethyl]-3-pyrrolidinyl}-2,2-acetonitrile salt of formula IV,

IV

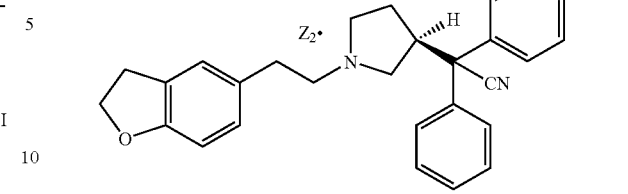

comprising: a) combining (S)-2,2-diphenyl-2-(3-pyrrolidinil)acetonitrile salt of formula III,

III

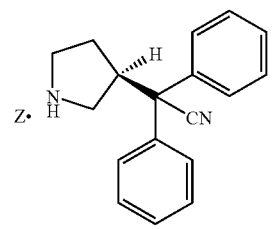

a compound of the formula V,

V

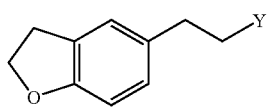

a solvent selected from the group consisting of a $C_{6-9}$ aromatic hydrocarbon, a polar organic solvent, water, and mixtures thereof, and a base to form a mixture; b) heating the mixture of step b, and c) reacting the mixture of step b with an acid to obtain to obtain a (S)-2-{1-[2-(2,3-dihydrobenzofuran-5-yl)ethyl]-3-pyrrolidinyl}-2,2-acetonitrile salt of formula IV; wherein $Z_1$ and $Z_2$ are independently an acid; wherein Y is a leaving group selected from the group consisting of I, Cl, Br, brosyl, mesyl, tosyl, trifluoroacetyl, and trifluoromethansulfonyl.

The invention encompasses a process for preparing Darifenacin hydrobromide of the following formula

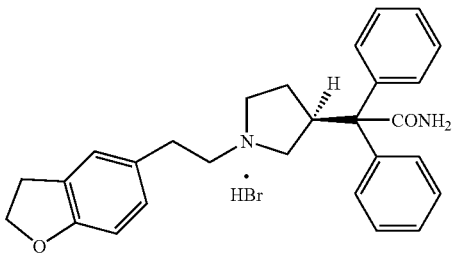

by a process comprising preparing a (S)-2-{1-[2-(2,3-dihydrobenzofuran-5-yl)ethyl]-3-pyrrolidinyl}-2,2-acetonitrile salt of formula IV by the process of the present invention, and converting it to Darifenacin hydrobromide.

The invention also encompasses another process for preparing darifenacin hydrobromide.

The process comprises: a) combining 3-(S)-(+)-hydroxypyrrolidine, a solvent selected from the group consisting of a $C_{6-9}$ aromatic hydrocarbon, a polar aprotic organic solvent, and mixtures thereof, a sulfonyl halide, and a base to obtain 1-X-sulfonyl-3-(S)-(−)-X-sulfonyloxypyrrolidine of formula I,

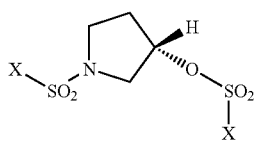

b) reacting the 1-X-sulfonyl-3-(S)-(−)-X-sulfonyloxypyrrolidine of formula I, diphenylacetonitrile, and an inorganic base, in an organic solvent selected from the group consisting of a $C_{6-9}$ aromatic hydrocarbon, a polar aprotic organic solvent, and mixtures thereof, to obtain (S)-2,2-diphenyl-2-(1-X-sulfonyl-3-pyrrolidinil)acetonitrile of formula II;

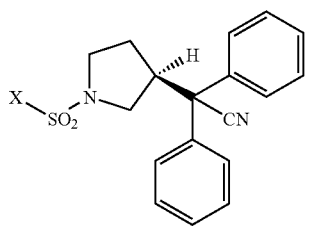

c) reacting the (S)-2,2-diphenyl-2-(1-X-sulfonyl-3-pyrrolidinil)acetonitrile intermediate of formula II, a bromine acceptor selected from the group consisting of phenol and naphthol, and an acid to obtain (S)-2,2-diphenyl-2-(3-pyrrolidinil) acetonitrile salt of formula III,

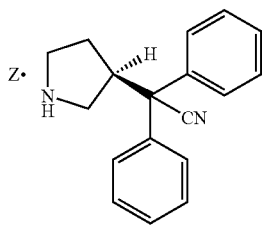

wherein the bromine acceptor is phenol only when the acid is HBr;

d) reacting the (S)-2,2-diphenyl-2-(3-pyrrolidinil)acetonitrile salt of formula III with an inorganic base in a solvent selected from the group consisting of a water immiscible organic solvent, a polar aprotic organic solvent, water and mixtures thereof to obtain a mixture;

e) acidifying the mixture of step d;

f) heating the mixture of step e;

g) basifying the mixture of step f to obtain 3-(S)-(+)-(1-carbamoyldiphenylmethyl)pyrrolidine of formula XI;

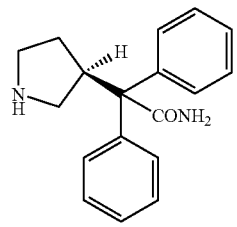

h) combining the 3-(S)-(+)-(1-carbamoyldiphenylmethyl) pyrrolidine of formula XI, 2-(2,3-dihydrobenzofuran-5-yl) acetaldehyde of formula XII,

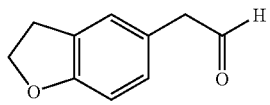

and a $C_{6-9}$ aromatic hydrocarbon to obtain a (S)-darifenamine of formula VII;

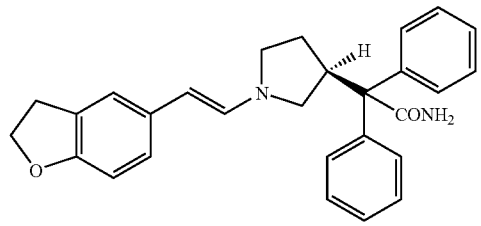

i) admixing the (S)-darifenamine of formula VII with a $C_{1-8}$ alcohol and a reducing agent to obtain the (S)-darifenacin of formula VIII; and

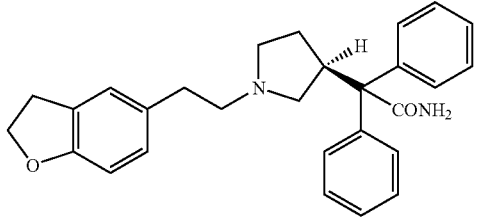

j) admixing the (S)-darifenacin of formula VIII with HBr to obtain darifenacin hydrobromide, wherein X is either $C_{1-10}$ alkyl or $C_{6-9}$ aryl, preferably, $C_{6-9}$ aryl, more preferably, tolyl, and $Z_1$ is an acid, preferably, either HBr or HCl.

The present further provides a process for the preparation of 2-(2,3-dihydrobenzofuran-5-yl)acetaldehyde of formula XII

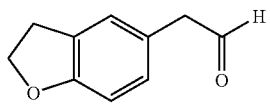
XII comprising: a) combining 2,3-dihydrobenzofura-5-yl-carboxyaldehyde of formula IX,

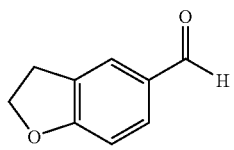
IX a C$_{2-4}$ alkylhaloacetate, an alkoxide, and an alkaline hydroxide to obtain the epoxide of the following formula;

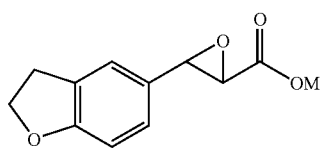

b) admixing the epoxide with a solvent selected from a group consisting of C$_{6-9}$ aromatic hydrocarbons, C$_{1-2}$ halogenated hydrocarbons, water, and mixtures thereof, and an acid selected from a group consisting of H$_3$PO$_4$, acetic acid, HCl sulfonic acid, and HBr to obtain 2-(2,3-dihydrobenzofuran-5-yl)acetaldehyde of formula XII.

The invention also encompasses 2-(2,3-dihydrobenzofuran-5-yl)acetaldehyde-bisulfite complex of formula X.

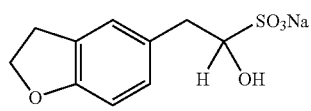
X

The invention also encompasses a process for purifying 2-(2,3-dihydrobenzofuran-5-yl)acetaldehyde of formula XII comprising: a) combining 2-(2,3-dihydrobenzofuran-5-yl) acetaldehyde, a water immiscible hydrocarbon, and Na$_2$S$_2$O$_5$ to form a mixture; and b) admixing with a base to the mixture to obtain purified 2-(2,3-dihydrobenzofuran-5-yl)acetaldehyde of formula XII.

The invention also encompasses (S)-darifenamine of formula VII

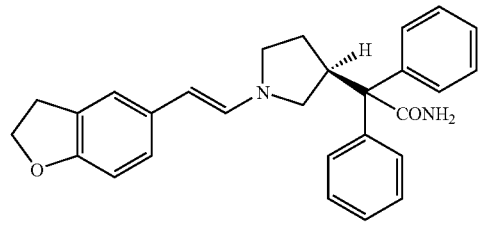
VII

The invention also encompasses a process for preparing (S)-darifenamine of formula VII

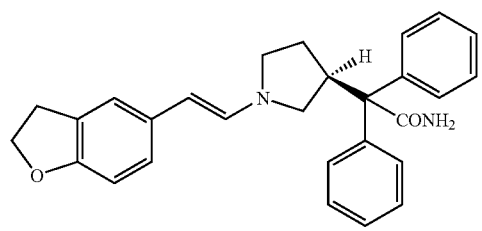
VII comprising: combining 3-(S)-(+)-(1-carbamoyldiphenylmethyl)pyrrolidine of formula XI,

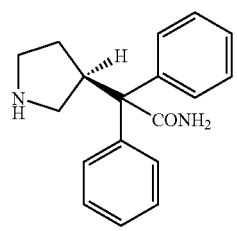
XI 2-(2,3-dihydrobenzofuran-5-yl)acetaldehyde of formula XII, and a C$_{6-9}$ aromatic hydrocarbon to form obtain (S)-darifenamine of formula VII.

The present invention further provides the use of the new compound, (S)-Darifenamine of formula VII for the preparation of (S)-Darifenacin hydrobromide.

The present invention also provides a process for the preparation of (S)-Darifenacin hydrobromide comprising preparing (S)-Darifenamine of formula VII by the process of the present invention, and converting it to (S)-Darifenacin hydrobromide.

The invention also encompasses a process for preparing the (S)-darifenacin of formula VIII

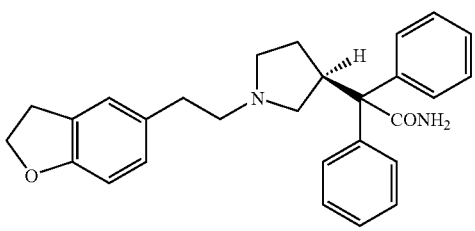

VIII comprising: combining (S)-darifenamine of formula VII,

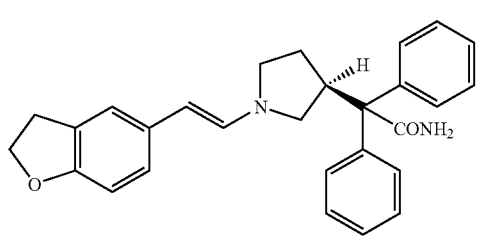

VII a $C_{1-8}$ alcohol, and a reducing agent to obtain to obtain (S)-darifenamine of formula VII.

The present invention provides a process for the preparation of (S)-Darifenacin hydrobromide comprising preparing (S)-Darifenacin by the process of the present invention, and converting it to (S)-Darifenacin hydrobromide.

The invention also encompasses a process for preparing oxidized darifenacin hydrobromide comprising combining an oxidized derivative of ethyl-dihydrobenzofuran of the following formula

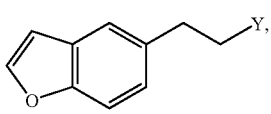

3-(S)-(+)-(1-carbamoyldiphenylmethyl)pyrrolidine of the formula IX

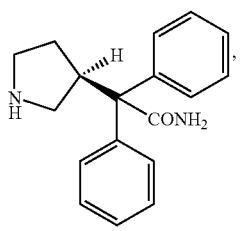

IX an inorganic base and water; admixing with HBr to obtain oxidized darifenacin hydrobromide; wherein Y is a leaving group selected from the group consisting of I, Cl, brosyl, mesyl, tosyl, trifluoroacetyl, and trifluoromethansulfonyl. Preferably, Y is Cl.

The invention also encompasses another process for the preparation of darifenacin hydrobromide comprising: a) combining an oxidized derivative of ethyl-dihydrobenzofuran of the following formula

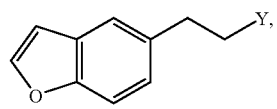

3-(S)-(+)-(1-carbamoyldiphenylmethyl)pyrrolidine of the formula IX

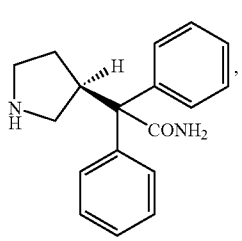

IX an inorganic base and water; b) admixing with HBr to obtain oxidized darifenacin hydrobromide, and c) admixing with a reducing agent to obtain darifenacin hydrobromide; wherein Y is a leaving group selected from the group consisting of I, Cl, brosyl, mesyl, tosyl, trifluoroacetyl, and trifluoromethansulfonyl. Preferably, Y is Cl.

The present invention encompasses a process for preparing Darifenacin hydrobromide by a process comprising preparing oxidized Darifenacin hydrobromide by the process of the present invention, and converting it to Darifenacin hydrobromide.

DETAILED DESCRIPTION OF THE INVENTION

The present invention relates to an improved process for preparing Darifenacin hydrobromide; wherein the cumbersome Mitsunobu reaction is avoided. Also, the synthesis can be scaled up, minimizing production hazards.

The invention encompasses a process for the preparation of darifenacin hydrobromide, comprising: a) combining 3-(S)-(+)-hydroxypyrrolidine, a solvent selected from the group consisting of a $C_{6-9}$ aromatic hydrocarbon, a polar aprotic organic solvent, and mixtures thereof, a sulfonyl halide, and a base to obtain 1-X-sulfonyl-3-(S)-(−)-X-sulfonyloxypyrrolidine of formula I,

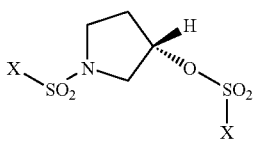

I b) reacting the 1-X-sulfonyl-3-(S)-(−)-X-sulfonyloxypyrrolidine of formula I, diphenylacetonitrile, and an inorganic base, in an organic solvent selected from the group consisting of a $C_{6-9}$ aromatic hydrocarbon, a polar aprotic organic solvent, and mixtures thereof, to obtain (S)-2,2-diphenyl-2-(1-X-sulfonyl-3-pyrrolidinil)acetonitrile of formula II;

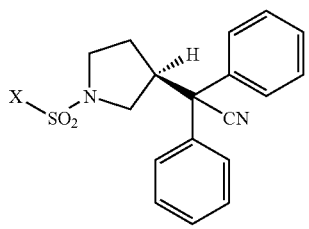

c) reacting the (S)-2,2-diphenyl-2-(1-X-sulfonyl-3-pyrrolidinil)acetonitrile intermediate of formula II, a bromine acceptor selected from the group consisting of phenol and naphthol, and an acid to obtain (S)-2,2-diphenyl-2-(3-pyrrolidinil) acetonitrile salt of formula III,

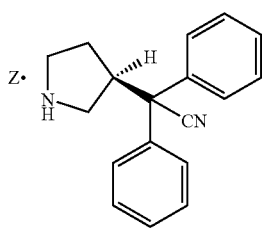

wherein the bromine acceptor is phenol only when the acid is HBr;

d) combining the (S)-2,2-diphenyl-2-(3-pyrrolidinil)acetonitrile salt of formula III, a compound of the formula V,

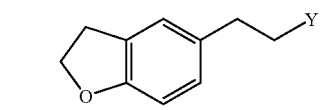

a solvent selected from the group consisting of a $C_{6-9}$ aromatic hydrocarbon, a polar organic solvent, water, and mixtures thereof, and a base to obtain a mixture;

e) heating the mixture of step d;

f) admixing the mixture of step d with an acid to obtain a (S)-2-{1-[2-(2,3 5-yl)ethyl]-3-pyrrolidinyl}-2,2-acetonitrile salt of formula IV; and

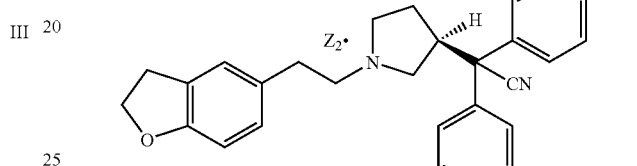

g) admixing the (S)-2-{1-[2-(2,3-dihydrobenzofuran-5-yl)ethyl]-3-pyrrolidinyl}-2,2-acetonitrile salt of formula IV, an inorganic base and a protic solvent; and h) reacting with hydrobromic acid to obtain darifenacin hydrobromide, wherein X is either $C_{1-10}$ alkyl or $C_{6-9}$ aryl, wherein Y is a leaving group selected from the group consisting of I, Cl, Br, mesyl, tosyl, brosyl, trifluoroacetyl, and trifluoromethansulfonyl, wherein $Z_1$ and $Z_2$ are independently an acid.

The process can be described by the following scheme:

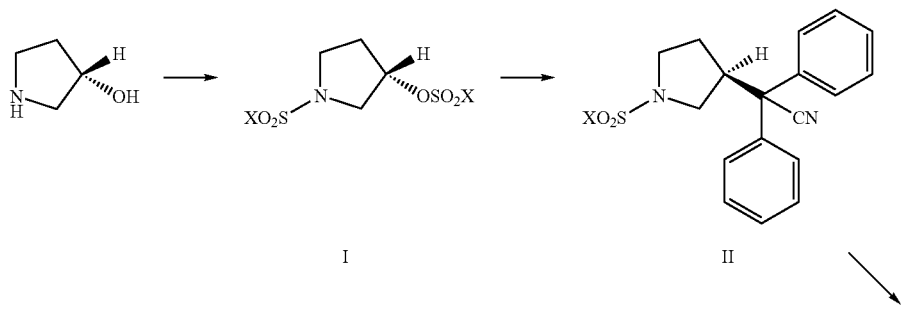

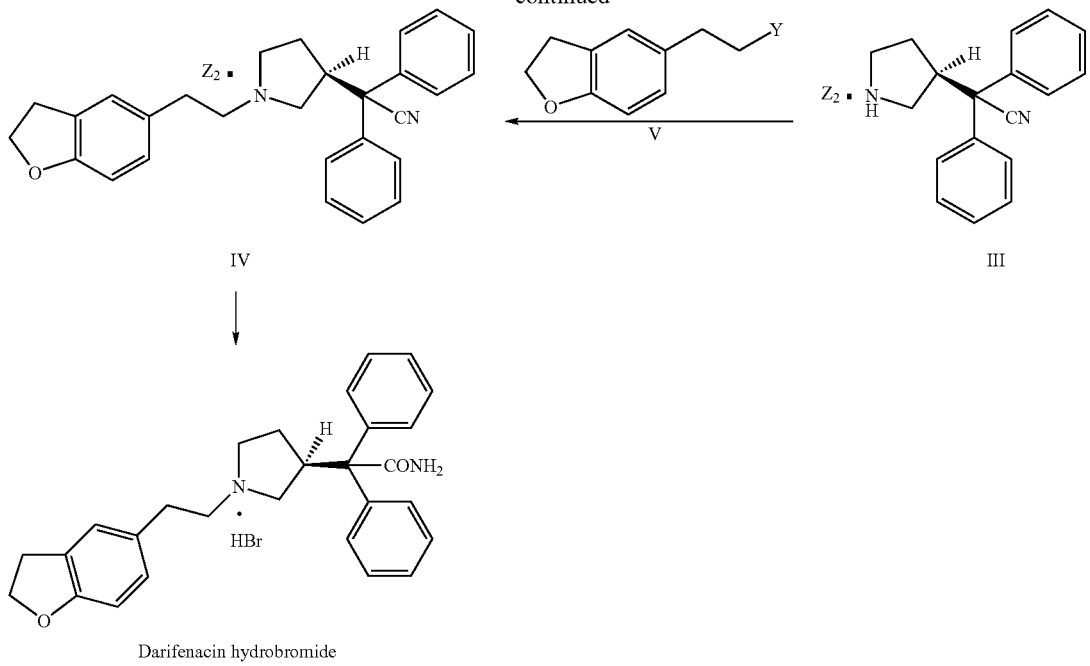

Darifenacin hydrobromide wherein X, Y, $Z_1$ and $Z_2$ are described before.

Preferably, X is $C_{6-9}$ aryl, more preferably, tolyl. Preferably, Y is Cl. Preferably, the acid, is either HBr or HCl.

The N—O-sulfonation reaction of the present invention is performed using solvents, which are not hazardous and toxic, as compared to pyridine that is used in U.S. Pat. No. 5,096,890. Also, the reaction is much shorter, and leads to a much higher yield, 96% vs. 75%. Moreover, the product is isolated very easily from a mixture of toluene and water, as compared to the difficult isolation performed in U.S. Pat. No. 5,096,890, which includes recovering the product by time consuming steps, such as distillation of pyridine, extractions with dichloromethane, and crystallization from n-propanol. Hence, the sulfonation reaction limits the process from being scaled up.

The intermediate of formula I, 1-X-sulfonyl-3-(S)-(−)-X-sulfonyloxypyrrolidine

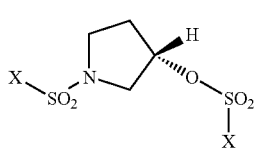

I is prepared by a process comprising combining 3-(S)-(+)-hydroxypyrrolidine of the following formula,

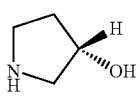

3-(S)-(+)-hydroxypyrrolidine a solvent selected from the group consisting of a $C_{6-9}$ aromatic hydrocarbon, a polar aprotic organic solvent, and mixtures thereof, a sulfonyl halide, and a base; wherein X is either $C_{1-10}$ alkyl or $C_{6-9}$ aryl. Preferably, X is $C_{6-9}$ aryl, and more preferably tolyl.

Typically, the 1-X-sulfonyl-3-(S)-(−)-X-sulfonyloxypyrrolidine of formula I is obtained by the above process in a purity of about 95% to about 99% area by HPLC.

The starting material, 3-(S)-(+)-hydroxypyrrolidine is commercially available.

Typically, combining the 3-(S)-(+)-hydroxypyrrolidine and the solvent provides a solution. The sulfonyl halide is then added to the solution to form a mixture. The addition of the sulfonyl halide to the solution leads to a rise in the temperature of the solution, typically to about 35° C. to about 40° C. Preferably, the base is then added to the mixture to form a reaction mixture, which leads to a second rise in temperature, typically to about 50° C. to about 60° C. Preferably, after the base is added, the reaction mixture is maintained at a temperature of about 25° C. to about reflux, more preferably, at about 50° C. to about 55° C. After the addition of the base, the reaction mixture is maintained for about 2 to about 10 hours, more preferably, for about 4 to about 6 hours.

Preferably, the $C_{6-9}$ aromatic hydrocarbon is toluene or o-, m-, or p-xylene. Preferably, the polar aprotic organic solvent is a $C_{1-10}$ halogenated aliphatic hydrocarbon, amide, or sulfoxide. A preferred $C_{1-10}$ halogenated aliphatic hydrocarbon is a $C_{1-5}$ halogenated hydrocarbon, and more preferably dichloromethane (referred to as DCM), 1,2,dichloroethane or dichloropentane. Preferably, the amide is either dimethylformamide (referred to as DMF) or dimethylacetamide (referred to as DMA). Preferably, the sulfoxide is a $C_{1-4}$ sulfoxide, and more preferably dimethylsulfoxide (referred to as DMSO). The more preferred solvent is toluene.

Optionally, a phase transfer catalyst (referred to as PTC) may be used to increase the reaction rate. When the solvent is a $C_{6-9}$ aromatic hydrocarbon, preferably, a phase transfer catalyst is used. Preferably, the PTC is added to the solution of 3-(S)-(+)-hydroxypyrrolidine prior to the addition of the sulfonyl halide. Preferably, the PTC is selected from the group consisting of tetrabutylammonium bromide, ALIQUAT® tributylmethylammonium chloride, tetrabutylammonium sulfate, and DMSO, and more preferably tetrabutylammonium bromide.

Preferably, the halide moiety of the sulfonyl halide is selected from chloride, bromide, and iodide, and more preferably chloride. Preferably, the sulfonyl halide is tosylchloride, mesylchloride, or brosylchloride, and more preferably tosylchloride. Preferably, the sulfonyl halide is added portion-wise.

Preferably, the base is either an inorganic base or an organic base. A preferred organic base is selected from the group consisting of aliphatic and aromatic amines. Preferably, the aliphatic amine is triethylamine, methylmorpholine, or N,N-diisopropylethyl amine. A preferred aromatic amine is pyridine. The inorganic base is added, preferably, in a form of an aqueous solution. The aqueous solution contains, preferably, an alkali base, and more preferably either sodium hydroxide or potassium hydroxide. Preferably, the base is added slowly, more preferably over about a half an hour to about two hours, and even more preferably over about one hour.

The process for preparing 1-X-sulfonyl-3-(S)-(–)-X-sulfonyloxypyrrolidine of formula I may further comprise a recovery step. The 1-X-sulfonyl-3-(S)-(–)-X-sulfonyloxypyrrolidine may be recovered by any method known to one of ordinary skill in the art. Such methods include, but are not limited to, adding water to the reaction mixture; cooling the reaction mixture to obtain a precipitate of the 1-X-sulfonyl-3-(S)-(–)-X-sulfonyloxypyrrolidine, and filtering the precipitate from the reaction mixture.

Preferably, the addition of water provides a suspension. Preferably, the suspension is cooled to a temperature of about 20° C. to about –5° C., and more preferably to about 5° C. to about 0° C., to induce precipitation of the 1-X-sulfonyl-3-(S)-(–)-X-sulfonyloxypyrrolidine. Preferably, the cooled suspension is maintained for at least about one hour, preferably, for about 1 to about 2 hours, to give a precipitate of 1-X-sulfonyl-3-(S)-(–)-X-sulfonyloxypyrrolidine. The precipitate is then filtered and dried.

The 1-X-sulfonyl-3-(S)-(–)-X-sulfonyloxypyrrolidine of formula I thus obtained may then be converted to (S)-2,2-diphenyl-2-(1-X-sulfonyl-3-pyrrolidinil)acetonitrile II.

The intermediate of formula II, (S)-2,2-diphenyl-2-(1-X-sulfonyl-3-pyrrolidinil)acetonitrile

II

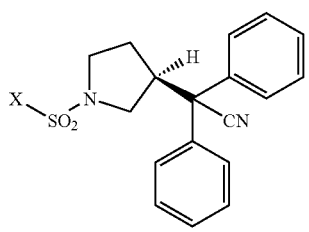

is prepared by a process comprising combining 1-X-sulfonyl-3-(S)-(–)-X-sulfonyloxypyrrolidine of formula I, diphenylacetonitrile, an organic solvent selected from the group consisting of a $C_{6-9}$ aromatic hydrocarbon, a polar aprotic organic solvent, and mixtures thereof, and an inorganic base; wherein X is either $C_{1-10}$ alkyl or $C_{6-9}$ aryl. Preferably, X is $C_{6-9}$ aryl, and more preferably tolyl.

(S)-2,2-diphenyl-2-(1-X-sulfonyl-3-pyrrolidinil)acetonitrile of the formula II is obtained by the above process in a purity of about 95% to about 99% area by HPLC, and more preferably about 99% to about 100% area by HPLC.

Typically, combining the diphenylacetonitrile and the organic solvent provides a first mixture. The addition of the inorganic base to the first mixture typically causes the temperature of the first mixture to rise to about 20° C. to about 40° C., and preferably to about 25° C. to about 35° C. Preferably, the first mixture is cooled to a temperature of about 30° C. to about 15° C., and more preferably to a temperature of about 25° C. to about 15° C., prior to the addition of the 1-X-sulfonyl-3-(S)-(–)-X-sulfonyloxypyrrolidine of formula I. Typically, the addition of the 1-X-sulfonyl-3-(S)-(–)-X-sulfonyloxypyrrolidine of formula I provides a second mixture. Preferably, the second mixture is heated to a temperature of about 50° C. to about 100° C., and more preferably to a temperature of about 70° C. to about 75° C. The heated second mixture is maintained, preferably, for about 3 to about 6 hours, and more preferably, for about 4 to about 5 hours.

Preferably, the $C_{6-9}$ aromatic hydrocarbon is toluene. Preferably, the polar aprotic organic solvent is either an amide or a sulfoxide. A preferred amide is a $C_{1-2}$ amide, and more preferably either DMF or DMA. A preferred sulfoxide is a $C_{1-4}$ sulfoxide, and more preferably DMSO. The more preferred organic solvent is DMF.

Preferably, the inorganic base is either a metal alkoxide or an alkali hydroxide. A preferred metal alkoxide is either sodium tert-butoxide or sodium methoxide. A preferred alkali hydroxide is either sodium or potassium hydroxide. The more preferred inorganic base is a metal alkoxide, most preferably either sodium or potassium tert-butoxide.

The process for preparing (S)-2,2-diphenyl-2-(1-X-sulfonyl-3-pyrrolidinil)acetonitrile of formula II may further comprise a recovery step. The recovery may be may be done by a process comprising adding to the second mixture to a mixture of water and a solvent selected from the group consisting of toluene, DCM, ethyl acetate (referred to as EtOAc), butyl acetate (referred to as BuOAc), and n-butanol to form a mixture having an aqueous and an organic phase; separating the aqueous and organic phases; washing the organic phase with water; and concentrating the organic phase under reduced pressure to obtain a concentrated residue. The residue is then cooled to a temperature of about 10° C. to about –10° C., and preferably to about 3° C. to about –3° C., to give a precipitate of (S)-2,2-diphenyl-2-(1-X-sulfonyl-3-pyrrolidinil)acetonitrile.

The (S)-2,2-diphenyl-2-(1-X-sulfonyl-3-pyrrolidinil)acetonitrile of formula II thus obtained may then be converted to S)-2,2-diphenyl-2-(3-pyrrolidinil)acetonitrile salt of formula III.

The intermediate of formula III, (S)-2,2-diphenyl-2-(3-pyrrolidinil)acetonitrile salt, is prepared by a process comprising heating a mixture comprising the compound of formula II, a bromine acceptor selected from phenol and naphthol and an acid, wherein the bromine acceptor is phenol only when the acid is HBr. Preferably, the mixture is heated to a temperature of about 80° C. to about 120° C., more preferably, to about 117° C. to about 120° C. Preferably, the heated mixture is maintained for about 1 hour to about 2 hours, more preferably, for about 1 hour to about 1.5 hours. Preferably, the acid is HBr, $H_2SO_4$, $H_3PO_4$, $HClO_4$, or $CF_3SO_3H$, and more preferably HBr. When using HBr as the acid, it is added in a form of an aqueous solution, having a concentration of about 30% to about 60%, more preferably, of about 48% to about 60%.

The (S)-2,2-diphenyl-2-(3-pyrrolidinil)acetonitrile salt of formula III may be recovered by a process comprising cooling the mixture to a temperature of about 30° C. to about 15°

C., more preferably, to a temperature of about 30° C. to about 25° C., followed by extracting with a $C_{1-10}$ halogenated aliphatic hydrocarbon, and washing with brine. The organic phase is concentrated under reduced pressure to give a residue containing the compound of formula III and the solvent. Preferably, the $C_{1-10}$ halogenated aliphatic hydrocarbon is a $C_{1-5}$ halogenated hydrocarbon, more preferably, a $C_{1-3}$ halogenated hydrocarbon. Most preferably, the $C_{1-3}$ halogenated hydrocarbon is selected from the group consisting of DCM, chloroform, dichloroethane, 1,1-dichloroethane, and 1,5-dichloropentane. The residue is then combined with a second solvent selected from the group consisting of BuOAc, toluene, acetone, 2-butanone, and diisopropylether, followed by a complete removal of the $C_{1-10}$ halogenated aliphatic hydrocarbon, preferably, by distillation, to give a second residue.

The second residue, containing the compound of formula III and a solvent selected form the group consisting of BuOAc, toluene, acetone, 2-butanone, and diisopropylether can be purified by a crystallization process from a solvent selected from the group consisting of $C_{1-10}$ ester, $C_{1-10}$ ketone, $C_{1-10}$ ether, $C_{1-10}$ aliphatic hydrocarbon, $C_{6-9}$ aromatic hydrocarbon, and mixtures thereof. Preferably, the $C_{1-10}$ ester is ethylacetate, n-butylacetate, i-butylacetate, or n-propylacetate, more preferably, ethylacetate. Preferably, the $C_{1-10}$ ketone is acetone, 2-butanone, methyl-isobutylketone, or cyclohexanone. A preferred $C_{1-10}$ ether is diethylether, diisopropylether, dibutylether, or methyl isobutylether. Preferably, the $C_{1-10}$ aliphatic hydrocarbon is pentane, hexanes, heptanes, or petroleum ether. Preferably, the $C_{6-9}$ aromatic hydrocarbon is toluene or xylenes. Preferably, a mixture of EtOAc and hexane is used.

The compound of formula III thus obtained may then be converted to (S)-2-{1-[2-(2,3-dihydrobenzofuran-5-yl)ethyl]-3-pyrrolidinyl}-2,2-acetonitrile salt of formula IV.

The intermediate of formula IV, (S)-2-{1-[2-(2,3-dihydrobenzofuran-5-yl)ethyl]-3-pyrrolidinyl}-2,2-acetonitrile salt,

IV

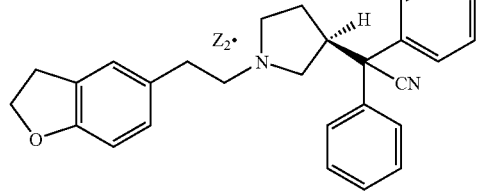

is prepared by a process comprising: a) combining (S)-2,2-diphenyl-2-(3-pyrrolidinil)acetonitrile salt of formula III,

III

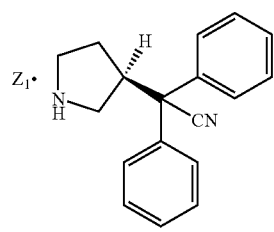

a derivative of ethyl-dihydrobenzofuran of the formula V,

V

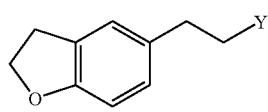

a solvent selected from the group consisting of a $C_{6-9}$ aromatic hydrocarbon, a polar organic solvent, water, and mixtures thereof, and a base to obtain a mixture; b) heating the mixture of step b; and c) reacting the mixture of step c with an acid; wherein $Z_1$ and $Z_2$ are independently an acid. Preferably, the acid is either HBr or HCl.

When $Z_1$ and $Z_2$ are HBr, the compound of formula III corresponds to (S)-2,2-diphenyl-2-(3-pyrrolidinil)acetonitrile-hydrobromide of the following formula,

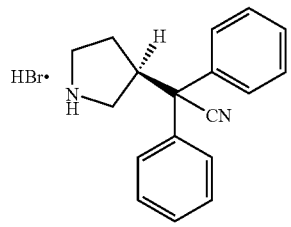

and the compound of formula IV corresponds to (S)-2-{1-[2-(2,3-dihydrobenzofuran-5-yl)ethyl]-3-pyrrolidinyl}-2,2-acetonitrile-hydrobromide of the following formula.

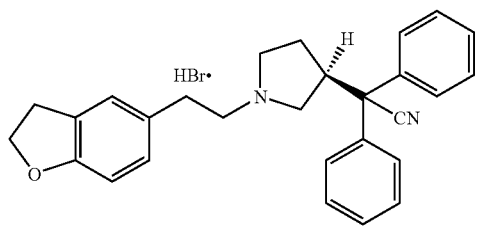

When $Z_1$ and $Z_2$ are HCl, the compound of formula III corresponds to (S)-2,2-diphenyl-2-(3-pyrrolidinil)acetonitrile-hydrochloride of the following formula,

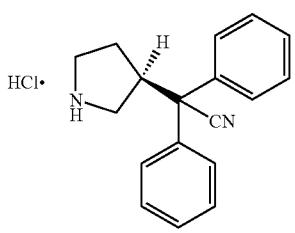

and the compound of formula IV corresponds to (S)-2-{1-[2-(2,3-dihydrobenzofuran-5-yl)ethyl]-3-pyrrolidinyl}-2,2-acetonitrile-hydrochloride of the following formula.

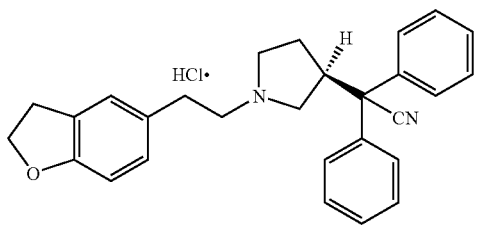

Typically, the base and the solvent are combined, initially, to obtain a first mixture. This mixture is then combined with (S)-2,2-diphenyl-2-(3-pyrrolidinil)acetonitrile salt of formula III, and with a derivative of ethyl-dihydrobenzofuran of the formula V, to obtain a a second mixture, the mixture of step a. Preferably, the mixture of step a is heated to a temperature of about 50° C. to about reflux, more preferably, to a temperature of about 75° C. to about 80° C. Preferably, the heated mixture is maintained for about 3 hours to about 7 hours, where the following compound,

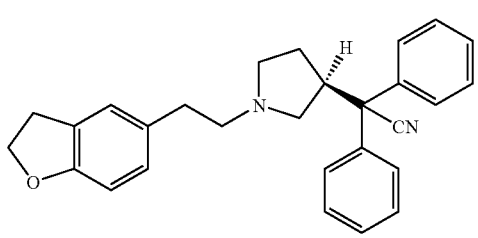

is expected to be formed. More preferably, the heated mixture is maintained for about 4 hours to about 5 hours. The above compound may be recovered before the addition of the acid.

Preferably, the base is either an inorganic base or an organic base. A preferred organic base is selected from the group consisting of aliphatic and aromatic amines. Preferably, the aliphatic amine is triethylamine, tribytulamine, methylmorpholine, pyridine, or N,N-diisopropylethyl amine. When an inorganic base is used, it is in the form of an aqueous solution. A preferred inorganic base is an alkali hydroxide, alkali carbonate, alkali bicarbonate, or alkoxide. A preferred alkali hydroxide is either sodium hydroxide or potassium hydroxide. Preferably, an alkali carbonate is sodium carbonate or potassium carbonate. Preferably, alkali bicarbonate is either sodium bicarbonate or potassium bicarbonate. A preferred alkoxide is either sodium methoxide or potassium methoxide. The more preferred base is an alkali hydroxide, even more preferably, sodium hydroxide.

Preferably, the $C_{6-9}$ aromatic hydrocarbon is toluene. A preferred polar organic solvent is an amide, a sulfoxide, or a nitrile. Preferably, the amide is either DMF or DMA. Preferably, the sulfoxide is DMSO. A preferred nitrile is acetonitrile (referred to as ACN). The more preferred solvent is water.

The reaction may be monitored by HPLC.
The following compound

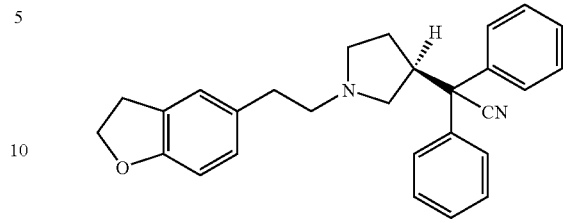

may be recovered by any method known to a skilled artisan. The recovery may comprise cooling the mixture of step c; extracting the cooled mixture with a solvent selected from the group consisting of EtOAc, BuOAc, toluene, and n-butanol; washing the extract with water; and evaporating the solvent. Preferably, the mixture is cooled to a temperature of about 30° C. to about 15° C.

Preferably, the following compound

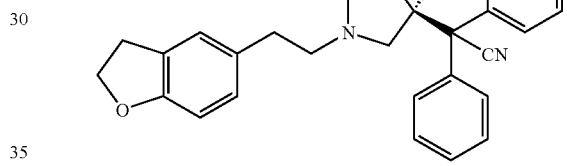

may be converted to the salt of formula IV directly, without isolation. When the conversion to the salt of formula IV is done directly, an acid is added to the organic phase, obtained by the above extractions, followed by cooling to a temperature of about 18° C. to about 15° C., to obtain a precipitate. The precipitate may be recovered by filtration, washing and drying.

The compound of formula V;

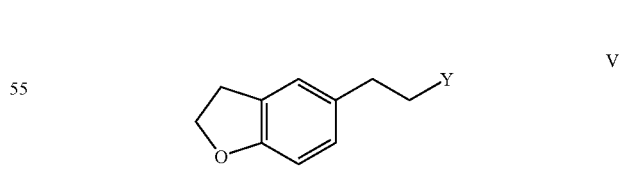

wherein Y is a leaving group selected from the group consisting of I, Cl, brosyl, Br, mesyl, tosyl, trifluoroacetyl, and trifluoromethansulfonyl, preferably, Cl, used to prepare (S)-2-{1-[2-(2,3-dihydrobenzofuran-5-yl)ethyl]-3-pyrrolidinyl}-2,2-acetonitrile salt of formula IV, can be prepared according to a process comprising: a) combining 2(2,3-dihydrobenzofura-5-y)-acetic acid of the following formula:

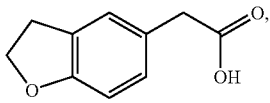

a $C_{1-4}$ alcohol, and a catalyst to obtain 2(2,3-dihydrobenzofura-5-y)-acetic acid methyl ester of the following formula;

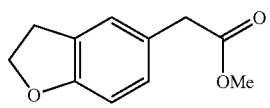

b) combining the 2(2,3-dihydrobenzofura-5-y)-acetic acid methyl ester a reducing agent and a $C_{4-6}$ alcohol to obtain 2(2,3-dihydrobenzofura-5-y)-ethanol of the following formula;

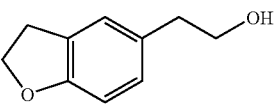

c) combining the 2(2,3-dihydrobenzofura-5-y)-ethanol, a solvent selected from the group consisting of a $C_{1-2}$ halogenated hydrocarbon, $C_{3-6}$ ester, and $C_{6-9}$ aromatic hydrocarbon, and a substance containing a leaving group selected from the group consisting of Cl, Br, mesyl, brosyl, tosyl, trifluoroacetyl, and trifluoromethansulfonyl to obtain the compound of formula V; wherein Y is a leaving group selected from the group consisting of I, Cl, brosyl, Br, mesyl, tosyl, trifluoroacetyl, and trifluoromethansulfonyl.

The starting 2(2,3-dihydrobenzofura-5-y)-acetic acid is commercially available.

Preferably, the $C_{1-4}$ alcohol, used in step a, is selected from the group consisting of methanol, ethanol, propanol, and butanol, and more preferably methanol. Optionally, a mixture of solvents may be used in step a. Preferably, the mixture is that of $C_{1-4}$ alcohol and toluene, and more preferably of methanol and toluene.

Preferably, the catalyst is an acid. Preferably, the acid is either an organic or an inorganic acid selected from the group consisting of sulfuric acid, p-toluenesulfonic acid, methanesulfonic acid, HCl, $HClO_4$, and $H_3PO_4$. More preferably, the acid is an inorganic acid, and even more preferably a mineral acid, and most preferably sulfuric acid.

The reaction between the 2(2,3-dihydrobenzofura-5-y)-acetic acid, the $C_{1-4}$ alcohol and the catalyst may be performed with heating. Preferably, the heating is done to a temperature of about 60° C. to about 70° C., and more preferably about 65° C. to about 70° C. Preferably, heating is done for about 1 to about 5 hours, and more preferably for about 2 to about 3 hours.

The reaction for preparing 2(2,3-dihydrobenzofura-5-y)-acetic acid methylester may further comprise a recovery step. The recovery may be done by any method known to a skilled artisan. According to the process of the present invention, the recovery comprises adding a base to the reaction mixture comprising 2(2,3-dihydrobenzofura-5-y)-acetic acid methylester; removing the solvent; adding a $C_{6-9}$ aromatic hydrocarbon; washing with a basic solution; and removing the solvent. Preferably, the base is sodium bicarbonate. Preferably, removing the solvent from the reaction mixture provides a residue. Preferably, the addition of a $C_{6-9}$ aromatic hydrocarbon to the residue provides a solution. Preferably, the $C_{6-9}$ aromatic hydrocarbon is toluene. Preferably, the basic solution is sodium bicarbonate.

Preferably, the $C_{4-6}$ alcohol, used in step b, is t-butanol. Preferably, a mixture of $C_{1-4}$ alcohol and $C_{4-6}$ alcohol may be used, in step b, instead of the $C_{4-6}$ alcohol alone. More preferably, the mixture is that of methanol and t-butanol.

Preferably, the reducing agent is a metal hydride. Preferably, the metal hydride is selected from the group consisting of $NaBH_4$, $LiAlH_4$, and VITRIDE® sodium dihydro-bis-(2-methoxyethoxy) aluminate. More preferably, the reducing agent is $NaBH_4$.

Combining the 2(2,3-dihydrobenzofura-5-y)-acetic acid methyl ester a reducing agent and a $C_{4-6}$ alcohol to obtain 2(2,3-dihydrobenzofura-5-y)-ethanol provides a suspension. Preferably, the suspension is heated to a temperature of about 65° C. to about 75° C., more preferably, of about 70° C. to about 75° C. Preferably, the $C_{1-4}$ alcohol is added drop-wise. Preferably, the drop-wise addition is done over a period of about 2 to about 6 hours, and more preferably over a period of about 5 to about 6 hours. Typically, adding the $C_{1-4}$ alcohol provides a mixture. Preferably, the mixture is maintained for a total time of about 5 to about 10 hours, and more preferably for about 5 to about 7 hours. If the reaction is not completed after 5 to about 10 hours, a second amount of a reducing agent can be added. Preferably, the reducing agent is added with a $C_{1-4}$ alcohol. After the addition of the reducing agent and a $C_{1-4}$ alcohol, the reaction is further maintained, preferably, for about 1 to about 14 hours, more preferably, for about 2 to about 3 hours.

The reaction for preparing 2(2,3-dihydrobenzofura-5-y)-ethanol may further comprise a recovery step. The recovery done by any method known to a skilled artisan. According to the process of the present invention, the recovery comprises removing the solvent; adding water and a solvent selected from the group consisting of toluene, dichloromethane, and ethyl acetate to obtain a mixture having an aqueous phase and an organic phase; separating the aqueous and organic phases; extracting the organic phase with water and a solvent selected from the group consisting of toluene, dichloromethane, and ethyl acetate; extracting the organic phase with water; and removing the solvent.

Preferably, the $C_{1-2}$ halogenated hydrocarbon is dichloromethane. A preferred $C_{3-6}$ ester is ethyl acetate, isopropylacetate, butylacetate, or isobutylacetate. Preferably, the $C_{6-9}$ aromatic hydrocarbon is toluene, xylenes, i-propylbenzene, or styrene. The preferred solvent is toluene.

Preferably, the substance containing a leaving group is selected from the group consisting of $SOCl_2$, $PCl_3$, $PCl_5$, $POCl_3$, tosylchloride, mesylchloride, brosylchloride, trifluoroacetyl chloride, and trifluoromethansulphonyl chloride. Preferably, the substance containing a leaving group is $SOCl_2$, $PCl_3$, $PCl_5$, or $POCl_3$, more preferably, $SOCl_2$. Preferably, the substance containing a leaving group is added drop-wise. When the substance containing a leaving group is one of tosylchloride, mesylchloride, brosylchloride, trifluoroacetyl chloride, and trifluoromethansulfonyl chloride, a base may also be used. Preferably, the base is either an organic or an inorganic base. The organic base may be, preferably, an aliphatic or aromatic amine. Preferably, the aliphatic amine is triethylamine, ethyldiisopropylamine, or N-methylmorpholine. A preferred aromatic amine is pyridine. The inorganic base is preferably either an alkali metal hydroxide or an alkali metal carbonate. Preferably, the alkali metal hydroxide is sodium hydroxide, potassium hydroxide, or cesium hydroxide. A preferred alkali metal carbonate is sodium, potassium, or cesium carbonate. The more preferred base is an organic base, preferably, triethylamine.

Preferably, combining the 2(2,3-dihydrobenzofura-5-y)-ethanol with a solvent selected from the group consisting of a $C_{1-2}$ halogenated hydrocarbon, $C_{3-6}$ ester, and $C_{6-9}$ aromatic hydrocarbon, a substance containing a leaving group provides a mixture. Preferably, the mixture is heated to a temperature of about 60° C. to about 80° C., more preferably, of about 60° C. to about 70° C. The mixture is, preferably, maintained, for about 12 to about 20 hours, more preferably, for about 15 to about 18 hours.

The process for preparing the derivative of ethyl-dihydrobenzofuran of the formula V may further comprise a recovery step. The recovery done by any method known to a skilled artisan. According to the process of the present invention, the recovery comprises cooling the reaction mixture to a temperature of about 30° C. to about 15° C., preferably, to about 25° C. to about 20° C., followed by adding the reaction mixture to a basic solution to form a mixture having an aqueous phase and an organic phase; separating the aqueous and organic phases; extracting the aqueous phase with toluene; washing the organic phase with water; removing the solvent; and decolorizing the obtained residue. Preferably, the basic solution is of sodium bicarbonate. Decolorization may be done by any method skilled in the art, such as using activated charcoal.

The recovered derivative of ethyl-dihydrobenzofuran of formula V may be purified by crystallization from methanol/water or methanol/water/acetone. The process comprises dissolving the derivative of ethyl-dihydrobenzofuran of formula V in methanol, and adding water or a mixture of water and acetone, followed by maintaining for about an hour to about 3 hours to promote crystallization of the derivative of ethyl-dihydrobenzofuran of formula V. The crystallized derivative of ethyl-dihydrobenzofuran of formula V is then filtered, washed and dried.

The process for preparing the compound of formula IV may further comprise a process for converting it to darifenacin bromide.

The transformation of the compound of formula IV to darifenacin hydrobromide comprises hydrolysis of the nitrile group; wherein the starting material can be the free base of the salt of formula IV or the salt of formula IV. The hydrolysis may be done by a process comprising: a) heating a suspension of an inorganic base in a protic solvent; b) adding the free base or the salt of formula IV to obtain a mixture; c) heating the mixture of step b, and d) adding HBr to the mixture of step c.

Preferably, the protic solvent is a $C_{1-10}$ alcohol. More preferably, the $C_{1-10}$ alcohol is selected from the group consisting of 2-methy-2-butanol, n-butanol, sec-butanol, n-pentanol, sec-amyl alcohol, and cyclohexanol. Most preferably, the $C_{1-10}$ alcohol is 2-methyl-2-butanol. Preferably, the inorganic base is an alkali base, more preferably, either NaOH or KOH, and most preferably, NaOH.

Preferably, the suspension is heated to a temperature of about 55° C. to about 70° C. Preferably, the heated suspension is maintained for about 1 to about 2 hours, more preferably, for about 1 to about 1.5 hours, prior to the addition of the free base or the salt of formula IV.

Preferably, the mixture is heated at a temperature of about 100° C. to about 110° C. Preferably, the heated mixture is maintained for about 20 to about 36 hours, more preferably, for about 30 to about 32 hours, prior to the addition of HBr.

The HBr may be added after work-up of the mixture. The work-up may be done by cooling the heated mixture to a temperature of about 25° C. to about 15° C., and further combining it with water to form a mixture comprising of an aqueous and an organic phase, followed by separating the aqueous and organic phases. The organic phase is then concentrated to give a residue, which is dissolved in a solvent selected from the group consisting of methylethylketone (referred to as MEK), n-butanol, EtOAc, BuOAc, acetone, and toluene. The solution is then filtered to eliminate undissolved particles, and the HBr is added to the filtrate.

Darifenacin hydrobromide may be recovered by concentrating the filtrate after the addition of HBr, to give solid foam, which is then slurried in a solvent selected from the group consisting of diisopropylether, MEK, n-butanol, EtOAc, BuOAc, acetone, and toluene.

The invention also encompasses another process for the preparation of darifenacin hydrobromide comprising: a) combining 3-(S)-(+)-hydroxypyrrolidine, a solvent selected from the group consisting of a $C_{6-9}$ aromatic hydrocarbon, a polar aprotic organic solvent, and mixtures thereof, a sulfonyl halide, and a base to obtain 1-X-sulfonyl-3-(S)-(-)-X-sulfonyloxypyrrolidine of formula I,

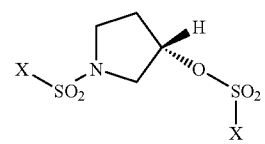

I b) reacting the 1-X-sulfonyl-3-(S)-(-)-X-sulfonyloxypyrrolidine of formula I, diphenylacetonitrile, and an inorganic base, in an organic solvent selected from the group consisting of a $C_{6-9}$ aromatic hydrocarbon, a polar aprotic organic solvent, and mixtures thereof, to obtain (S)-2,2-diphenyl-2-(1-X-sulfonyl-3-pyrrolidinil)acetonitrile of formula II;

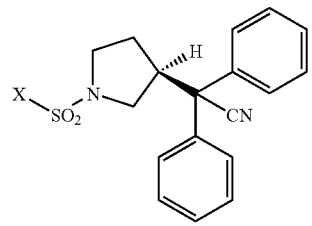

II c) reacting the (S)-2,2-diphenyl-2-(1-X-sulfonyl-3-pyrrolidinil)acetonitrile intermediate of formula II, a bromine acceptor selected from the group consisting of phenol and naphthol, and an acid to obtain (S)-2,2-diphenyl-2-(3-pyrrolidinil) acetonitrile salt of formula III,

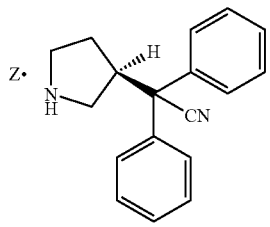

III wherein the bromine acceptor is phenol only when the acid is HBr d) reacting the (S)-2,2-diphenyl-2-(3-pyrrolidinil)acetonitrile salt of formula III with an inorganic base in a solvent selected from the group consisting of a water immiscible organic solvent, a polar aprotic organic solvent, water and mixtures thereof to obtain a mixture;

e) acidifying the mixture of step d;

f) heating the mixture of step e;

g) basifying the mixture of step f to obtain 3-(S)-(+)-(1-carbamoyldiphenylmethyl)pyrrolidine of formula XI;

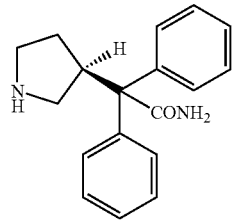

XI h) combining the 3-(S)-(+)-(1-carbamoyldiphenylmethyl) pyrrolidine of formula XI, 2-(2,3-dihydrobenzofuran-5-yl) acetaldehyde of formula XII,

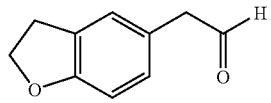

XII and a $C_{6-9}$ aromatic hydrocarbon to obtain a (S)-darifenamine of formula VII;

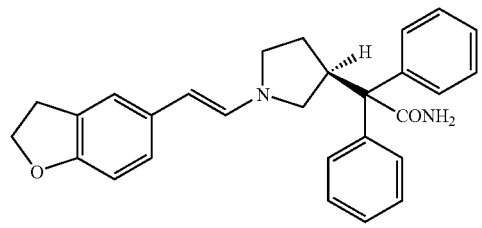

VII i) admixing the (S)-darifenamine of formula VII with a $C_{1-8}$ alcohol and a reducing agent to obtain the (S)-darifenacin of formula VIII; and

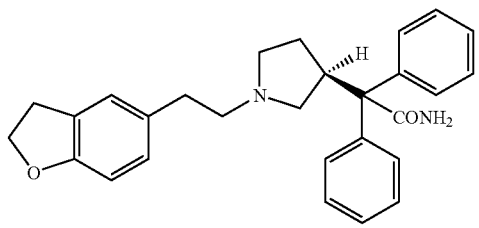

VIII j) admixing the (S)-darifenacin of formula VIII with HBr to obtain darifenacin hydrobromide, wherein X is either $C_{1-10}$ alkyl or $C_{6-9}$ aryl, wherein $Z_1$ is an acid. Preferably, X is $C_{6-9}$ aryl, more preferably, tolyl. Preferably, the acid is either HBr or HCl.

The process can be described by the following scheme:

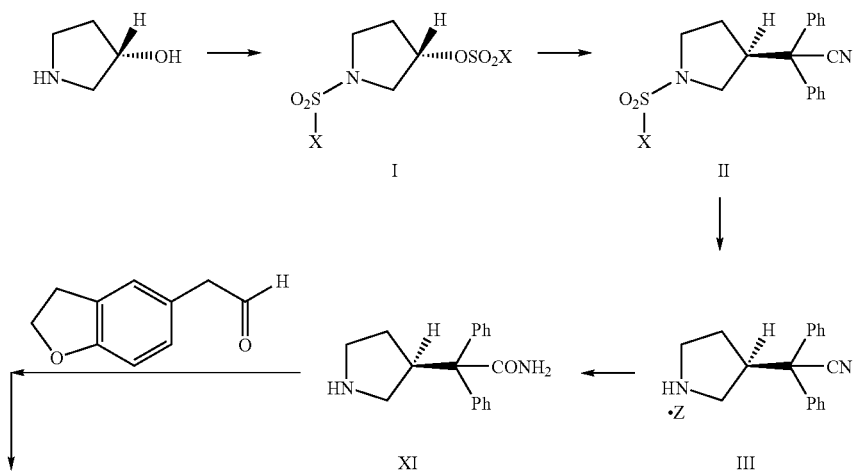

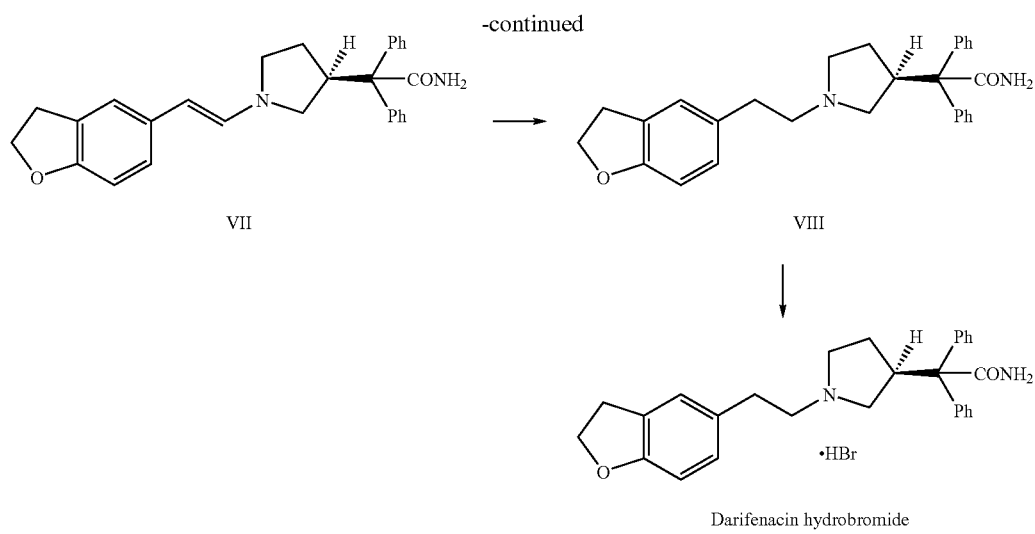

VII → VIII → Darifenacin hydrobromide wherein X is either $C_{1-10}$ alkyl or $C_{6-9}$ aryl, preferably, $C_{6-9}$ aryl, more preferably, tolyl, and Z is an acid, preferably, either HBr or HCl.

The intermediates of formulas I, II, and III may be prepared by the processes described above.

The intermediate of formula XI

XI is prepared by combining (S)-2,2-diphenyl-2-(3-pyrrolidinil) acetonitrile salt of formula III,

III a solvent selected from the group consisting of a water immiscible organic solvent, a polar aprotic organic solvent, water, and mixtures thereof, and an inorganic base, wherein $Z_1$ is an acid. Preferably, $Z_1$ is either HBr or HCl.

Preferably, the water immiscible organic solvent is either a $C_{6-9}$ aromatic hydrocarbon or a $C_{1-10}$ halogenated aliphatic hydrocarbon. A preferred $C_{1-10}$ halogenated aliphatic hydrocarbon is $C_{1-5}$ halogenated aliphatic hydrocarbon, more preferably, DCM. Preferably, the sulfoxide is $C_{2-5}$ sulfoxide, more preferably, DMSO. Preferably, the ester is $C_{2-5}$ ester, more preferably, EtOAc. A preferred ketone is $C_{3-6}$ ketone, more preferably, MEK. Preferably, the nitrile is $C_{2-4}$ nitrile, more preferably, ACN. Preferably, the $C_{6-9}$ aromatic hydrocarbon is $C_{6-9}$ aromatic hydrocarbon, more preferably, toluene. Preferred mixtures are either that of toluene and water or that of DCM and water. The more preferred solvent is water.

Preferably, the inorganic base is an aqueous solution of an alkali base. A preferred alkali base is alkali hydroxide, alkali carbonate, or alkali bicarbonate. Preferably, the alkali hydroxide is either sodium hydroxide or potassium hydroxide. Preferably, the alkali carbonate is either sodium carbonate or potassium carbonate. A preferred alkali bicarbonate is either sodium bicarbonate or potassium bicarbonate. The more preferred base is alkali hydroxide, most preferably, sodium hydroxide.

The intermediate, 3-(S)-(+)-(1-carbamoyldiphenylmethyl) pyrrolidine of formula XI, is then converted to (S)-darifenamine of formula VII.

The invention also encompasses (S)-darifenamine of formula VII.

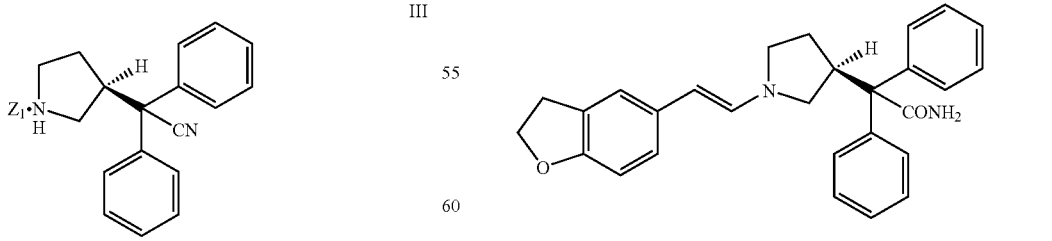

VII

The new compound, (S)-Darifenamine of formula VII can be used for the preparation of (S)-Darifenacin hydrobromide.

The intermediate (S)-darifenamine of formula VII is prepared by a process comprising: combining 3-(S)-(+)-(1-carbamoyldiphenylmethyl)pyrrolidine of formula XI,

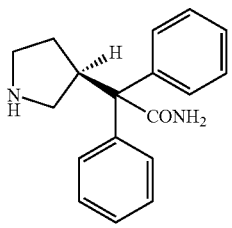

2-(2,3-dihydrobenzofuran-5-yl)acetaldehyde of formula XII,

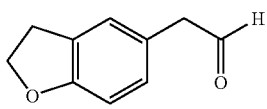

and a $C_{6-9}$ aromatic hydrocarbon.

Typically, combining 3-(S)-(+)-(1-carbamoyldiphenylmethyl)pyrrolidine, the compound of formula XI, 2-(2,3-dihydrobenzofuran-5-yl)acetaldehyde of formula XII, and a $C_{6-9}$ aromatic hydrocarbon provides a mixture. Preferably, the mixture is maintained at a temperature of about 0° C. to about 70° C., more preferably, at a temperature of about 10° C. to about 40° C. Preferably, the mixture is maintained for about 3 hours to about 20 hours, more preferably, for about 10 hours to about 15 hours.

Preferably, the $C_{6-9}$ aromatic hydrocarbon is selected from the group consisting of toluene, xylene, or trimethylbenzene, and more preferably toluene.

The 2-(2,3-dihydrobenzofuran-5-yl)acetaldehyde of formula XII

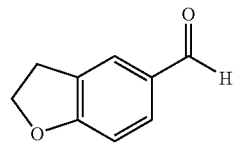

is prepared by a process comprising: a) combining 2,3-dihydrobenzofura-5-yl-carboxyaldehyde of formula IX,

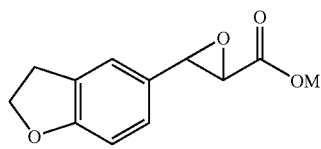

a $C_{2-4}$ alkylhaloacetate, an alkoxide, and an alkaline hydroxide to obtain the epoxide of the following formula;

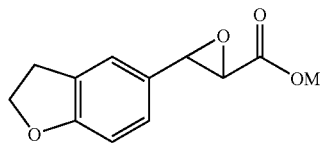

b) admixing the epoxide with a solvent selected from a group consisting of $C_{6-9}$ aromatic hydrocarbons, $C_{1-2}$ halogenated hydrocarbons, water, and mixtures thereof, and an acid selected from a group consisting of $H_3PO_4$, acetic acid, HCl sulfonic acid, and HBr to obtain 2-(2,3-dihydrobenzofuran-5-yl)acetaldehyde of formula XII.

Usually, combining the compound of formula IX and a $C_{2-4}$ alkylhaloacetate provides a solution. Preferably, the solution is heated to a temperature of about 30° C. to about 60° C., more preferably, to about 45° C. to about 50° C., prior to the addition of the alkoxide.

Preferably, the $C_{2-4}$ alkylhaloacetate is 2-butylchloroacetate.

Preferably, the alkoxide is t-butoxide. The alkoxide may be solid or a solution in an alcohol. Preferably, the alcohol is 2-butanol. Preferably, the alkoxide is added portion-wise. Preferably, the solution of the alkoxide is added over a period of about 0.5 hour to about 1.5 hours, more preferably, for about 45 minutes to about 1 hour. Preferably, the alkoxide is added at a temperature of about 30° C. to about 60° C., more preferably, for about 45° C. to about 50° C. Preferably, a suspension is obtained.

Preferably, the obtained suspension is added slowly to the alkaline hydroxide, providing a mixture. Preferably, the obtained suspension is added to the alkaline hydroxide over a period of about 1 to about 4 hours, and, more preferably, about 1 to about 2 hours. Preferably, the alkaline hydroxide is selected from a group consisting of NaOH, KOH, LiOH, and more preferably, KOH. The alkaline hydroxide may be solid or an aqueous solution, preferably, an aqueous solution. Preferably, the addition is done at a temperature of about 30° C. to about 60° C., more preferably, for about 45° C. to about 50° C.

Preferably, after the addition, the mixture is maintained for about 0.5 hour to about 1.5 hours, more preferably, for about 45 minutes to about 1 hour, thus leading to a thick suspension comprising the epoxide of the following formula;

wherein M is an alkali metal. Preferably, M is selected from a group consisting of Na, K, and Li, more preferably, K.

Preferably, the solvent is added to the thick suspension, comprising of the epoxide forming a new mixture. The new mixture is cooled. Preferably, the new mixture is cooled to a temperature of about 10° C. to about 0° C., more preferably, to about 5° C. to about 1° C.

Preferably, the $C_{6-9}$ aromatic hydrocarbon is toluene. A preferred $C_{1-2}$ halogenated hydrocarbon is dichloromethane. The more preferred solvent is toluene.

After cooling, an acid selected from a group consisting of $H_3PO_4$, acetic acid, HCl, sulfonic acid and HBr is added. Preferably, the acid is $H_3PO_4$. Preferably, the acid is added drop-wise. Preferably, the drop-wise addition is done for about 15 minutes to about 2 hours. Preferably, the addition of the acid results in a pH of about 5 to about 7, more preferably, about 5.4 to about 5.8. The addition of the acid causes the suspension to transform to a two phase solution having an aqueous and an organic phase comprising the aldehyde of formula XII.

The process for preparing the 2-(2,3-dihydrobenzofuran-5-yl)acetaldehyde of formula XII may further comprise a recovery process. The recovery may be done by any method known to a skilled artisan. The recovery may be done by a process comprising: separating the phases, washing the organic phase with water and then with a saturated NaCl solution, followed by removing the solvent from the organic phase.

The invention also encompasses 2-(2,3-dihydrobenzofuran-5-yl)acetaldehyde-bisulfite complex of formula X.

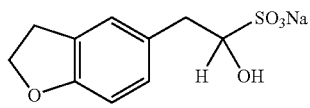

The bisulfite complex can be used to purify the aldehyde of formula XII. The process comprises a) combining 2-(2,3-dihydrobenzofuran-5-yl)acetaldehyde, a water immiscible hydrocarbon, and $Na_2S_2O_5$ to form a mixture; and b) admixing with a base to the mixture to obtain purified 2-(2,3-dihydrobenzofuran-5-yl)acetaldehyde of formula XII.

Preferably, the water immiscible hydrocarbon is either a $C_{6-9}$ aromatic hydrocarbon or a saturated hydrocarbon. Preferably, the $C_{6-9}$ aromatic hydrocarbon is toluene. The more preferred solvent is toluene.

$Na_2S_2O_5$ may be used in a solid form or in a form of an aqueous solution. Preferably, $Na_2S_2O_5$ is used in a form of an aqueous solution.

Preferably, the mixture obtained is maintained at a temperature of about 15° C. to about 35° C., more preferably, at about 20° C. to about 25° C. Preferably, the mixture is maintained for about 2 hours to about 4 hours.

The bisulfite complex can also be used for preparing the compound of formula V. The process for the preparation of derivatives of ethyl-dihydrobenzofuran of the formula

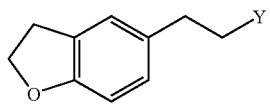

V, from the bisulfite complex comprises combining the bisulfite complex of formula X,

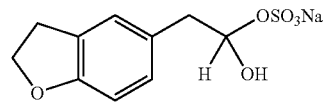

water, NaOH, $Na_2CO_3$, a water immiscible hydrocarbon, and a reducing agent to form a mixture comprising of the alcohol of the following formula;

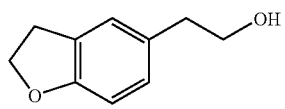

and combining the mixture with a solvent selected from the group consisting of $C_{1-2}$ halogenated hydrocarbons, $C_{3-6}$ esters, and $C_{6-9}$ aromatic hydrocarbons, and a substance containing a leaving group selected from the group consisting of Cl, Br, mesyl, brosyl, tosyl, trifluoroacetyl, and trifluoromethansulfonyl to obtain the compound of formula V, wherein Y is a leaving group selected from the group consisting of I, Cl, brosyl, Br, mesyl, tosyl, trifluoroacetyl, and trifluoromethansulfonyl, preferably, Cl.

Preferably, NaOH is added to a suspension of the compound of formula X in water to obtain a basic mixture comprising 2-(2,3-dihydrobenzofuran-5-yl)acetaldehyde of formula XII. Preferably, the pH of the basic mixture is about 9 to about 11, more preferably about 9.5 to about 10.5, and even more preferably about 10 to about 10.2.

Preferably, after adjusting the pH, $Na_2CO_3$ and a water immiscible hydrocarbon are added to obtain a mixture. Preferably, the water immiscible hydrocarbon is either a $C_{6-9}$ aromatic hydrocarbon or a saturated hydrocarbon. Preferably, the $C_{6-9}$ aromatic hydrocarbon is toluene. A preferred saturated hydrocarbon is either heptane or cyclohexane. The more preferred solvent is toluene.

Preferably, the mixture is cooled to a temperature of about 20° C. to about 0° C., more preferably to about 10° C. to about 5° C., prior to the addition of the reducing agent. Adding a reducing agent provides a reaction mixture. Preferably, the reducing agent is selected from the group consisting of $NaBH_4$, $LiAlH_4$, and $H_2$/Pd. A solution or solid $NaBH_4$ may be used. Preferably, a solution of $NaBH_4$ is used. Preferably, the $NaBH_4$ is in solution in water or an alcohol. Preferably, the alcohol is a $C_{3-6}$ alcohol. The more preferred solvent is water.

Preferably, the solution of the reducing agent is added drop-wise. Preferably, the drop-wise addition is done over a period of about 0.5 hour to about 1.5 hours, and more preferably over about 45 to about 60 minutes.

Preferably, a pH of about 9 to about 11, more preferably, about 9.8 to about 10.2 is maintained during the addition.

Preferably, after the addition of the reducing agent, the temperature was raised to about 10° C. to about 25° C., more preferably, to about 15° C. to about 25° C. Preferably, after raising the temperature, the reaction mixture is maintained for about 0.5 hour to about 1.5 hours, more preferably, for about 1 hour, leading to the corresponding alcohol of the following formula.

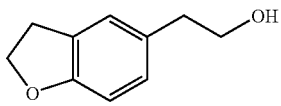

Preferably, the transformation of the alcohol to the compound of formula V is as described before.

The process for preparing (S)-darifenamine of formula VII may further comprise a process for converting it to (S)-darifenacin hydrobromide.

The conversion of (S)-darifenamine of formula VII to (S)-darifenacin hydrobromide may be done through the intermediate, (S)-darifenacin of formula VIII.

The intermediate (S)-darifenacin of formula VIII

VIII

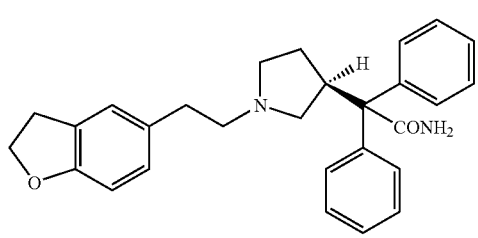

is prepared by a process comprising combining (S)-Darifenamine of formula VII,

VII

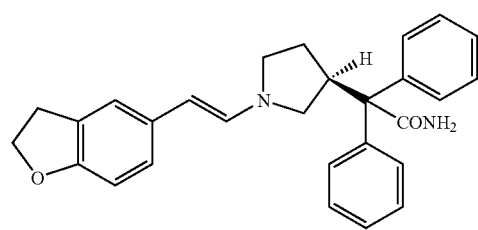

a $C_{1-8}$ alcohol, and a reducing agent to obtain (S)-darifenacine of formula VIII.

(S)-Darifenacin of formula VIII may be prepared step-wise or in one step, i.e., without isolation of (S)-Darifenamine of formula VII. Preferably, (S)-Darifenacin of formula VIII is prepared in one step.

Preferably, the reducing agent is added to a reaction mixture comprising (S)-Darifenamine of formula VII.

Preferably, the reducing agent is selected from the group consisting of $NaBH_4$, $LiAlH4$, and $H_2/Pd$ and more preferably $NaBH_4$. Preferably, a solution of $NaBH_4$ in the $C_{1-8}$ alcohol is used.

Preferably, the $C_{1-8}$ alcohol is selected from the group consisting of methanol, ethanol, propanol, isopropanol, butanol, isobutanol, pentanol, and hexanol. The more preferred $C_{1-8}$ alcohol is ethanol.

Preferably, the reducing agent is added portion-wise to a mixture of (S)-Darifenamine and the alcohol, to obtain a reaction mixture. Preferably, the portion-wise addition is done over a period of about 15 minutes to about 1 hour, and more preferably for about 20 to about 30 minutes.

After the portion-wise addition is complete, the reaction mixture is maintained for about 2 hours to about 10 hours, more preferably, for about 2 hours to about 4 hours. Preferably, the mixture is maintained at a temperature of about 0° C. to about 50° C., more preferably, about 10° C. to about 30° C. The reaction may be monitored by HPLC. Preferably, the formation of (S)-Darifenacin is monitored by HPLC.

The process for preparing (S)-Darifenacin of formula VIII may further comprise a recovery step. The recovery may be done according to a process known to a skilled artisan. The recovery may be done by washing the reaction mixture with water, followed by removing the solvent.

The (S)-darifenacin of formula VIII may then be converted to (S)-darifenacin hydrobromide, for example, according to the process disclosed in U.S. Pat. No. 5,096,890.

Preferably, (S)-darifenacin is converted to (S)-darifenacin hydrobromide by a process comprising: adding an aqueous solution of HBr to a solution of (S)-darifenacin in n-butanol, followed by removing the water to obtain a suspension. The suspension is cooled to induce precipitation of the (S)-darifenacin hydrobromide, and the precipitate of (S)-darifenacin hydrobromide is then collected by filtration.

The invention also encompasses a process for preparing oxidized darifenacin hydrobromide comprising combining an oxidized derivative of ethyl-dihydrobenzofuran of the following formula

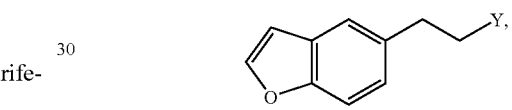

3-(S)-(+)-(1-carbamoyldiphenylmethyl)pyrrolidine of the formula IX

IX

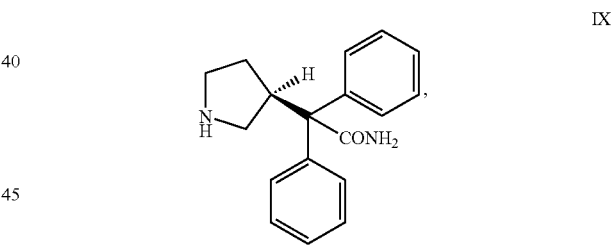

an inorganic base and water; admixing with HBr to obtain oxidized darifenacin hydrobromide; wherein Y is a leaving group selected from the group consisting of I, Cl, brosyl, mesyl, tosyl, trifluoroacetyl, and trifluoromethansulfonyl. Preferably, Y is Cl.

The invention also encompasses another process for the preparation of darifenacin hydrobromide comprising: a) combining an oxidized derivative of ethyl-dihydrobenzofuran of the following formula

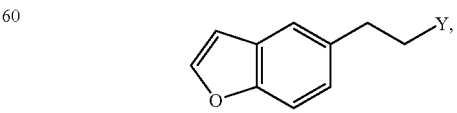

3-(S)-(+)-(1-carbamoyldiphenylmethyl)pyrrolidine of the formula IX

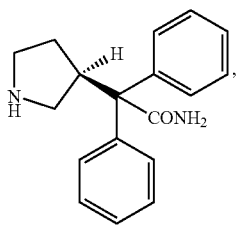

IX an inorganic base and water; b) admixing with HBr to obtain oxidized darifenacin hydrobromide; and c) admixing with a reducing agent to obtain darifenacin hydrobromide; wherein Y is a leaving group selected from the group consisting of I, Cl, brosyl, mesyl, tosyl, trifluoroacetyl, and trifluoromethansulfonyl. Preferably, Y is Cl.

Preferably, the inorganic base is $K_2CO_3$, $Na_2CO_3$, or $Cs_2CO_3$.

Preferably, after combining all the above substances, the combination is heated to reflux temperature, more preferably to about 100-120° C. Typically, the combination is heated to induce the formation of oxidized Darifenacin. Preferably, the combination is heated to for about 5 hours to about 10 hours.

After obtaining Darifenacin oxide, a work-up of the heated reaction mixture is done. The work-up is done, prior to admixing with HBr. Preferably, the work-up comprises: cooling the heated combination; admixing with $C_{4-8}$ alcohol, providing a solvent system comprising of at least a two-phases; separating the phases, and concentrating the organic phase.

Preferably, the heated combination is cooled to a temperature of about 90° C. to about 60° C., more preferably, to 90° C. to about 85° C. Preferably, the $C_{4-8}$ alcohol is n-butanol i-butanol, amylalcohol, cyclohexanol, or t-butanol. The solvent system having at least two-phases comprises an aqueous phase and an organic phase. After separating the phases, preferably, the organic phase is concentrated by distillation. Preferably, the concentrated organic phase is admixed with acetic anhydride, prior to the admixing with HBr. The addition of HBr provides a precipitate of oxidized darifenacin hydrobromide.

The process for preparing oxidized Darifenacin hydrobromide may further comprise recovering the oxidized Darifenacin hydrobromide. The recovery can be done by any process known to a skilled artisan. Preferably, the recovery comprises filtering the precipitate, washing and drying.

The process for preparing the oxidized Darifenacin hydrobromide may further comprise converting oxidized Darifenacin hydrobromide to Darifenacin hydrobromide. The conversion can be done, for example, according to the process disclosed in Example 8 of U.S. Pat. No. 5,096,890 (reproduced below as Comparative Example 24).

Typically, oxidized Darifenacin hydrobromide is reduced by reacting with a reducing agent providing Darifenacin hydrobromide. Preferably, the reaction of oxidized Darifenacin hydrobromide and the reducing agent is done in the presence of an acid. Preferably, the acid is acetic acid. Preferably, the reducing agent is selected from the group consisting of $NaBH_4$, $LiAlH_4$, and $H_2$/catalyst and more preferably, the reducing agent is a combination of a catalyst and hydrogen gas. Preferably, the catalyst is palladium, platinum, ruthenium, rhodium, or nickel. More preferably, the palladium is absorbed on charcoal.

Typically, the reaction is done under heating. Preferably, the heating is to a temperature of about 45° C. to about 50° C. Preferably, the hydrogen gas is present at atmospheric pressure.

Preferably, the reaction is maintained for about 6 to about 7 wherein the formation of Darifenacin hydrobromide is expected.

The process for preparing Darifenacin hydrobromide may further comprise a recovery step. The recovery can be done by any process known to a skilled artisan. Preferably, the recovery is done by filtering the catalyst; concentrating the filtrate; admixing the concentrated filtrate with n-butanol and HBr to obtain a mixture, and concentrating the mixture to obtain a precipitate of Darifenacin hydrobromide.

Preferably, the mixture is concentrated to obtain a filtrate having less than 1% of water.

The obtained precipitate can be isolated by filtration, washing and drying.

Having described the invention with reference to certain preferred embodiments, other embodiments will become apparent to one of ordinary skill in the art from consideration of the specification. The invention is further defined by reference to the following examples. It will be apparent to those of ordinary skill in the art that many modifications, both to materials and methods, may be practiced without departing from the scope of the invention.

EXAMPLES

Example 1

Preparation of 1-tosyl-3-(S)-(−)tosyloxypyrrolidine (Formula I)

(S)-3-pyrrolidinol (30 g, 0.344 moles) was dissolved in toluene (150 ml) and tetrabutylammonium bromide (3.39 g, 0.0105 moles) was added to the solution. p-Toluensulfonylchloride (140.94 g, 0.7393 moles) was then added portionwise to the solution, causing the temperature of the solution to rise to 35 to 40° C. Then, 30% NaOH (112.1 g, 0.8407 moles) was slowly added to the solution over about 1 hour, causing the temperature of the solution to rise to 55 to 60° C. After maintaining the solution for 5 hours at 55-60° C., the reaction was complete. Water (30 ml) was then added, and the resulting suspension was cooled to 0° C. over 1 hour to give a solid. The solid was filtered and washed with cold toluene and water to give the title compound. (Dry weight 127.95 g, yield 94%, HPLC purity 99.2% area). The main impurity is 1-tosyl-3-(S)-pyrrolidinol (reaction intermediate) in an amount of 0.05% area by HPLC.

Example 2

Preparation of (S)-2,2-diphenyl-2-(1-tosyl-3-pyrrolidinil)acetonitrile (Formula II)

Diphenylacetonitrile (63.7 g, 0.3296 moles) was dissolved in DMF (395 ml), followed by adding sodium tert-butylate (31.75 g, 0.33 moles), which caused the temperature of the solution to rise to 35° C. After cooling the solution to 20° C., 1-tosyl-3-(S)-(−)tosyloxypyrrolidine (126.5 g, 0.3198 moles) was added. The solution was warmed to 70 to 75° C., and, after maintaining the solution at 70 to 75° C. for 4 hours, the reaction was complete. Water (250 ml) and toluene (500 ml) were then added to the solution to form a two phase mixture having an aqueous and an organic phase. The phases were stirred at 70° C. and separated. The aqueous phase was extracted with toluene (50 ml), followed by washing the combined organic phases three times with water (100 ml each), and concentrating under vacuum to give a 250 ml residual volume. The residual volume was cooled to 0° C. to obtain a precipitate. The precipitate was filtered and washed with toluene and water to give the title compound. (Dry weight 116 g, yield 86.5%, and HPLC purity 99.3% area). The main impurities present are residual starting materials: diphenylacetonitrile and N—O-ditosyl-3-(S)-pyrrolidinol in amounts of 0.1% area by HPLC each.

Example 3

Preparation of (S)-2,2-diphenyl-2-(3-pyrrolidinil) acetonitrile hydrobromide(S-DIPACP.HBr) (Formula III)

In a 2 l reactor equipped with mechanical stirrer, thermometer and condenser load under nitrogen HBr 48% (1.100 ml), Phenol (44.08 g), S-DIPACP-N-Tosyl [(S)-2,2-diphenyl-2-(1-tosyl-3-pyrrolidinil)acetonitrile] (220 g) were loaded under nitrogen. The suspension was warmed to reflux (118-120° C.) to obtain a biphasic system. After 1 hr, the reaction was complete (residual starting material 0.33%). The reaction mixture was then cooled to 25-30° C. and dichloromethane (478 ml) was added. After stirring (5 min) the phases were separated (organic phase is upper layer) and the aqueous phase was extracted with dichloromethane (100 ml) and the phases again separated (organic phase is upper layer). The collected organic phases were concentrated to 280-290 ml by solvent distillation at atmospheric pressure obtaining an oily residue ($T_{int}$ 64° C.). Maintaining internal temperature at 65-70° C. ethylacetate (287 ml) was slowly added to the residue. (It is necessary to maintain temperature and to add ethyl acetate slowly to avoid sudden product crystallization). Distillation was continued at atmospheric pressure to reach a volume of 380-390 ml ($T_{int}$ 80° C., $T_{head}$ 70° C.). Ethyl acetate (191 ml) was added to the obtained suspension and distillation was continued at atmospheric pressure to reach a volume of 380-390 ml ($T_{int}$ 84° C., $T_{head}$ 72° C.). Repeated distillations are necessary to eliminate as much dichloromethane as possible in such a way as to increase yield. The suspension was cooled at 50-55° C. and ethyl acetate (300 ml) was added. The suspension was cooled to 20-25 ° C. and after 1 hr, was cooled to −7-8° C. After 2 hrs, the suspension was filtered and washed three times with cold ethyl acetate (95 ml) each. After washings, the product became white (initially it was pink). The wet product was dried under vacuum at 50-55° C. for 6-7 hrs to obtain the title compound. (Dry weight 166.3 g, yield 87.4%, HPLC purity 99.93% area).

Example 4

(S)-2,2-diphenyl-2-(3-pyrrolidinil)acetonitrile hydrobromide using β-Naphtol as bromine acceptor (Formula III)

(S)-2,2-diphenyl-2-(1-tosyl-3-pyrrolidinil)acetonitrile (5 g, 0.0120 moles) was added to 48% HBr (25 ml) together with β-naphtol (1.73 g, 0.0120 moles), to give a suspension. The suspension was warmed to reflux (117-120° C.), and, after 1 hour the reaction was complete. After cooling to 30° C., dichloromethane (10 ml) was added, and the mixture was stirred for 5 minutes. The phases were separated, and the aqueous phase was extracted with dichloromethane (5 ml). The combined organic phases were washed with saturated solution of NaCl, and then concentrated under vacuum to give a residual volume of 10 ml.

Ethyl acetate (10 ml) was added to the residual volume, and the distillation was continued at atmospheric pressure until a residual volume of 8 ml was obtained. Ethyl acetate was added, and the distillation continued until the dichloromethane was eliminated (residual volume 8 ml). Ethyl acetate (15 ml) and hexane (10 ml) were added to give a suspension. The suspension was cooled to 0° C. for 2 hours to give a precipitate that was filtered and washed with ethyl acetate to give the title compound. (Dry weight 3.0 g; yield 72.4%).

Example 5

Preparation of (S)-2-{1-[2-(2,3-dihydrobenzofuran-5-yl)ethyl]-3-pyrrolidinyl}-2.2-acetonitrile hydrobromide (Formula III)

Potassium carbonate (14.94 g, 0.1081 moles) was dissolved in water (45 ml), followed by adding (S)-2,2-diphenyl-2-(3-pyrrolidinil)acetonitrile hydrobromide (18.55 g, 0.0540 moles) and 5-(2-bromoethyl)-2,3-dihydrobenzo[2,3-b]furan (13.5 g, 0.05945 moles) to give a suspension. The suspension was warmed to 75° C., and, after 4 hours, the reaction was considered to be complete (unreacted starting material 1.5% area by HPLC). The heterogeneous mixture was cooled to 25° C. and ethyl acetate (100 ml) was added. After stirring, the phases were separated, the organic layer was washed with water, and the phases separated. 48% hydrobromic acid (9.6 g, 0.05668 moles) was added, and (S)-2-{1-[2-(2,3-dihydrobenzofuran-5-yl)ethyl]-3-pyrrolidinyl}-2,2-acetonitrile hydrobromide was crystallized from the suspension. The suspension was cooled to 15-18° C. for one hour, and the precipitate was filtered and washed with ethyl acetate to give the title compound. (Dry weight 23.8 g; yield 89.93%).

Example 6

Preparation of 3-(S)-(−)-(1-carbamoyl-1,1-diphenylmethyl)-1-[2-(2,3-dihydrobenzofuran-5-yl)ethyl] pyrrolidine hydrobromide (Formula III)

KOH (1.95 g, 0.03134 moles) was added to 2-methyl-2-butanol (7 ml), to obtain a suspension. The suspension was warmed to 60° C. for 1 hour, followed by adding (S)-2-{1-[2-(2,3-dihydrobenzofuran-5-yl)ethyl]-3-pyrrolidinyl}-2,2-acetonitrile hydrobromide (1 g, 0.00204 moles), and warming the reaction mixture (suspension) to reflux for 21-22 hours. After cooling, water (5 ml) was added to the reaction mixture to form a two-phase mixture, and the phases were separated. The solvent was distilled from the organic phase under vacuum, and a residue (0.900 g) was obtained and dissolved in methylethylketone (3 ml). The solution was filtered to eliminate undissolved solid, and 48% HBr (0.344 g, 0.00204 moles) was added. The solvent was distilled under vacuum, and a solid foam was obtained. The foam was slurried in diisopropylether, filtered, and washed to give the title compound. (Dry weight 0.750 g; yield 72%).

Example 7

Preparation of 3-(S)-(+)-(1-carbamoyl-1,1-diphenylmethyl)pyrrolidine Tartrate (Formula VI)

3-(S)-(+)-(1-Cyano-1,1-diphenylmethyl)pyrrolidine hydrobromide (80 g 0.2330 moles) was converted into its corresponding free base by treating with dichloromethane (400 ml), water (150 ml) and 30% NaOH (35 g). After phase separation and evaporation of the solvent from the organic phase, an oil residue was obtained. The oil residue was added to 90% $H_2SO_4$ (130 ml), and the mixture was heated to 100° C. for 17 hours. After cooling, the mixture was neutralized with sulfuric acid until a pH of 12 was obtained. The product was extracted with dichloromethane (250 ml). After washings with water, the solvent was evaporated by distillation, and the product was obtained as a foam (45.7 g). The foam was dissolved in 96% ethanol (460 ml), and L-Tartaric acid (26.9 g) was added, followed by cooling to 0° C., to induce crystallization of the tartrate salt. The salt was filtered after 1 hour, and washed with 96% ethanol to give the title compound. (Dry weight 64.5 g; yield 64.5%).

Example 8

Preparation of 3-(S)-(+)-(1-carbamoyl-1diphenylmethyl)pyrrolidine Tartrate (Formula VI)

a) Free Base Preparation

A four necked round bottomed flask equipped with a thermometer, mechanical stirrer and condenser was charged, under $N_2$, with 3-(S)-(+)-(1-carbamoyl-1,1-diphenylmethyl)pyrrolidine hydrobromide (96 g), Dichloromethane (280 ml), and water (20 ml). The temperature was maintained at 25-30° C. during the loading of NaOH 30% (41.2 g). The obtained heterogeneous system was stirred for 5 min. and the phases were separated. The organic phase was washed with water (41.2 ml), and the phases were separated. The organic phase was concentred under vacuum until a final volume of 120 ml was obtained.

b) Hydrolysis Reaction

A four necked round bottomed flask equipped with thermometer, mechanical stirrer and condenser to eliminate dichloromethane by distillation, was charged under $N_2$ with $H_2SO_4$ 90% (180 ml).

The sulfuric acid solution was warmed to 50-55° C., and the organic solution obtained above (120 ml) was added slowly allowing dichloromethane elimination by distillation. During the addition the mixture was warmed continuously to maintain an internal temperature of 60-65° C. When dichloromethane distillation stopped, the internal temperature was raised to 98-102° C. allowing residual dichloromethane elimination by distillation. Then, the temperature was maintained at 98-102° C. for 14-14.5 hrs.

The reaction mixture was cooled to 25-30° C. and added slowly to a mixture of NaOH 30% (958.3 g), water (720 g), and toluene (480 ml), allowing the internal temperature to reach 55-60° C. After stirring at 55-60° C. the phases were separated at 55-60° C. The aqueous phase was been extracted at 55-60° C. with toluene (160 ml).

The collected organic phases, maintained at 60-65° C., were washed at 60-65° C. with water 240 ml, and then n-butanol (200 ml), water (20 ml) and L-tartaric acid (42.05 g) were added to the separated organic phase at 45-65° C. The mixture was stirred at 45-65° C. until the L-tartaric acid was almost completely dissolved. At the same time a formation of a salt was detected, at the beginning as a white oil, and then as white solid. The suspension was cooled to 15-25° C. and filtered after two hours. When the suspension was too sticky it was found useful to warm to 60-65° C. and after 10-15 min to cool to 15-25° C. and filter. The cake was washed three times with n-butanol (50 ml each), and after 15 hrs of drying at 50-55° C. under vacuum 107 g of the title compound was obtained. (Yield: 88.9%. HPLC purity: 99.88% area).

Example 9

Preparation of 2(2,3-Dihydrobenzofura-5-y)acetic acid, methyl ester

98% $H_2SO_4$ (2 g) was added to a solution of 2(2,3-Dihydrobenzofura-5-y)acetic acid (200 g) in MeOH (500 ml), and the mixture was refluxed for 3 hrs (TLC: $SiO_2$, toluene/AcOEt 8:2; starting material not detected). After cooling to room temperature, $NaHCO_3$ (6.7 g) was added to the reaction mixture, and the solvent was distilled off at atmospheric pressure (about 440 ml), to give a light pink oily residue.

The oily residue was dissolved in toluene (250 ml), and washed with $NaHCO_3$ 6% (50 ml). After the phases were separated, the solvent was eliminated under vacuum distillation to obtain a light pink oily residue (227 g).

Example 10

Preparation of 2(2,3-Dihydrobenzofura-5-y)ethanol

2(2,3-Dihydrobenzofura-5-y)acetic acid, methyl ester (227 g residue) was dissolved in t-BuOH (600 ml), and then $NaBH_4$ (46.8 g) was added. The suspension was warmed to reflux and methanol (100 ml) was added very slowly in about 6 hrs maintaining reaction mixture at reflux. After the methanol addition, the reaction was maintained at reflux for half an hour (in process control revealed complete ester transformation). 400 ml of the t-BuOH-MeOH mixture was distilled off at atmospheric pressure. Water (400 ml) was added to residue and the distillation continued until $T_{int}$=93° C. and $T_{head}$=83° C. Water (400 ml) was added, and the distillation continued until $T_{int}$=96° C. and $T_{head}$=96° C. The reaction mixture was cooled to 70-75° C. and toluene (300 ml) was added. The separated organic phase was washed with water (100 ml) and NaCl 15% (100 ml). After the solvent was eliminated under vacuum distillation, an oily residue (176.8 g) of the title compound was obtained. The residue solidified upon cooling.

Example 11

2(2,3-Dihydrobenzofuran-5-y)ethylchloride $SOCl_2$ (74.7 g) was added to a solution of 2(2,3-Dihydrobenzofura-5-y)ethanol 80 g in toluene (400 ml) while maintaining the temperature below 25° C. The reaction mixture was stirred at 60° C. for 14 h and then cooled to room temperature. A reaction sample was quenched into 10% $Na_2CO_3$ (Residual 2(2,3-Dihydrobenzofura-5-y)ethanol 0.6% area by HPLC), and the pH was adjusted to 10-11 (measured on aqueous phase) by addition of 10% NaOH (about 480 ml) while maintaining the temperature below 30° C. The organic phase was separated. The aqueous phase was extracted with toluene (50 ml). The collected organic phases were washed twice with $H_2O$ (100 ml each) and anhydrified under vacuum distillation (residual pressure 40-50 mm Hg, $T_{int}$ 50-55° C.). To the organic phase, 20 g of TONSIL® silicate decolorizing agent and 4.2 g of ANTICHROMOS charcoal were added, stirred for 30 min at room temperature, filtered off and washed with toluene (2×30 ml), the decolorized solution was concentrated under vacuum (residual pressure 40-50 mm Hg, $T_{int}$ 50-55° C.) to eliminate toluene. Water (25 ml) was added to obtain a residue, and the residual toluene was eliminated by azeotropic distillation under vacuum (residual pressure 40-50 mm Hg, $T_{int}$ 50-55° C.). This residue was dissolved in methanol (373 ml) and charcoal (2 g) were added. After 20 minutes at 50-55° C. charcoal was filtered off and washed with hot methanol (2×10 ml). The obtained decolorized solution was cooled at 20-30° C., and 2(2,3-Dihydrobenzofuran-5-y) ethylchloride crystallized in the suspension. Water (280 ml) was added to the suspension at 25-30° C. over about 60 min to obtain a sticky, but stirrable, suspension. After 1 hr at 20-25° C. the solid was filtered, and washed three times with MeOH-Water 1:1 (20 ml each). The wet solid was dried at 35-40° C. max for 15 hrs to give the title compound. (Dry weight 81.8 g. Yield 92%. HPLC purity 99.2% area).

Example 12

Preparation of (S)-darifenacin hydrobromide

A 50 ml reactor was loaded with -(S)-(+)-(1-carbamoyl-1,1-diphenylmethyl)pyrrolidine Tartrate (4 g, 9.29 mmoles), 2(2,3-Dihydrobenzofuran-5-y)ethylchloride (1.95 g, 10.68 mmoles), potassium carbonate (6.14 g, 44.42 mmoles), and water (12.5 ml), to obtain a heterogeneous mixture. The heterogeneous mixture was heated to reflux (103° C.) for 2.5 hours. After cooling, dichloromethane, EtOAc or BuOAc (15 ml) were added, and, after stirring, the phases were separated. Acetic anhydride (0.5 ml) was added to the organic phase, and, after 1 hour at room temperature, the residual 3-(S)-(+)-(1-carbamoyl-1,1-diphenylmethyl)pyrrolidine was transformed into N-Acetyl derivative. The solvent was removed by distillation, and n-butanol (25 ml) was added to the residue. 48% hydrobromic acid (1.72 g) was also added, and the residual DCM was removed under vacuum distillation. In the case of EtOAc or BuOAc, distillation under vacuum is useful to eliminate water. Darifenacin hydrobromide crystallized, and, after cooling to room temperature, the darifenacin hydrobromide was filtered and washed. (Wet solid 4.17 g).

Example 13

Preparation of (S)-darifenacin hydrobromide

A 50 ml reactor was loaded with (S)-(+)-(1-carbamoyl-1,1-diphenylmethyl)pyrrolidine free base (2.6 g, 9.29 mmoles), 2(2,3-Dihydrobenzofuran-5-y)ethylchloride (1.95 g, 10.68 mmoles), potassium carbonate (6.14 g, 44.42 mmoles), and water (12.5 ml) to obtain a heterogeneous mixture. The heterogeneous mixture was heated to reflux (103° C.) for 2 to 5 hours. After cooling, dichloromethane, Ethyl acetate, or Butylacetate (15 ml) was added, and, after stirring, the phases were separated. Acetic anhydride (0.5 ml) was added to the organic phase, and, after 1 hour at room temperature, the residual 3-(S)-(+)-(1-carbamoyl-1,1-diphenylmethyl)pyrrolidine was transformed into N-Acetyl derivative (as described in example 11). Half of the solvent was removed by distillation, and n-butanol (25 ml) was added to the residue. 48% hydrobromic acid (1.72 g) was also added, and the residual DCM was removed under vacuum distillation. In the case of EtOAC or BuOAc, distillation under vacuum is useful to eliminate water. Darifenacin hydrobromide crystallized, and, after cooling to room temperature, the darifenacin hydrobromide was filtered and washed. (Dry solid 2.5 g).

Example 14

Preparation of (S)-darifenacin hydrobromide

A 150 ml reactor was loaded with water (37.5 ml), potassium carbonate (12 g), and 2(2,3-Dihydrobenzofuran-5-yl-ethylchloride (DBF-EtCl) (5.48 g). The mixture was warmed to 60-65° C. and DBF-EtCl melted. Then, (S)-(+)-(1-carbamoyl-1,1-diphenylmethyl)pyrrolidine tartrate (12 g) was loaded and the heterogeneous mixture was warmed to reflux (101-102° C.) for 5 hrs.

The reaction mixture was cooled to 80-85° C. and n-butanol (60 ml) was added. The internal temperature was maintained at 75-80° C., and the mixture was stirred until complete dissolution was obtained. Then, the mixture was cooled to 25-30° C. and the phases were separated. The organic phase was washed twice with water (30 ml) and the phases were separated.

Water was removed by vacuum distillation until a residual volume of 60 ml was obtained, and then n-butanol (30 ml) was added. Then, acetic anhydride (0.6 ml) was loaded and the mixture was stirred at 20-30° C. for 1 hr, followed by loading HBr 48% (4.7 g) at 25-27° C. The water and 20 ml of butanol were removed by vacuum distillation to obtain a suspension of darifenacin hydrobromide. The suspension was stirred at 25-30° C. for 2 hrs, and then cooled to 0-5° C., and filtered after 1 hr. The cake was washed with cold n-Butanol (3×3 ml), and dried under vacuum at 50-55° C. for 6-7 hrs. (Dry weight 11.2-11.5. Yield 79-81%).

Example 15

Crystallization of (S)-darifenacin hydrobromide

A 100 ml reactor was loaded with crude darifenacin hydrobromide (10 g), n-butanol (70 ml), and charcoal (0.3 g). The mixture was warmed to reflux to obtain a solution. The charcoal was filtered at reflux and washed with n-butanol (5 ml).

The solution was maintained at 100° C. and seeded to induce crystallization. After 30 min at 100° C., the mixture was cooled to 0° C. over 3 hrs, and after 1 hr at 0° C. the mixture was filtered. The product was washed with cold butanol (3×3 ml). (Dry weight 8.8-8.9 g. Yield 88-89%. HPLC purity 99.65-99.75% area).

Example 16

Preparation of (S)-darifenacin hydrobromide via (S)-darifenamine 3-(S)-(+)-(1-Carbamoyl-1,1-diphenylmethyl)pyrrolidine (2.1 g, 7.5 mmoles) and 2,3-dihydrobenzofuran-5-yl,acetaldehyde (1.4 g, 8.6 mmoles) were combined with toluene (20 ml) at room temperature, and reacted for 15 hours to give (S)-darifenamine.

At this point, a solution of $NaBH_4$ (0.57 g, 15 mmoles) in ethanol (10 ml) was added slowly, and after 3 hours at room temperature, HPLC analysis revealed formation of (S)-Darifenacin. After washing with water, the solvent was eliminated by distillation, and the obtained residue was dissolved in n-BuOH followed by the addition of HBr 48% (1.5 g, 9 mmoles). Water was eliminated under vacuum, and a slow crystallization was observed. After cooling, the product was filtered and washed with n-BuOH to give the title compound. (Dry weight 0.7 g).

The same reaction has been performed in presence of molecular sieves and titanium isopropylate with similar results.

Example 17

Purification of Darifenacin HBr

The product of Example 16 (3.6 g) was suspended in n-Butanol (25 ml), and heated to reflux to obtain a solution. Charcoal (0.1 g) was added, and, after 5 minutes at reflux, was filtered off. After cooling to room temperature, Darifenacin HBr was filtered, washed, and dried at 45-50° C. under vacuum for 10 hours. (Dry solid 3.20 g; overall yield 68%; HPLC purity 99.86% area).

Example 18

2,3-Dihydrobenzofura-5-yl, acetaldehyde

In a four necked round bottomed flask equipped with thermometer, mechanical stirrer and condenser, was charged under $N_2$, 2,3-Dihydrobenzofura-5-yl, carboxaldehyde (50 g, 0.33 moles) and 2-butylchloroacetate (66.5 g, 0.4415 moles). The solution was warmed to 40-45° C., followed by a drop-wise addition (in about 1 hour) of 288 ml of 17% (w/v) potassium 2-butylate solution in 2-butyl alcohol (0.43 moles). The reaction was maintained at a temperature of 40-45° C., and after 1 hour at 40-45° C., HPLC analysis revealed almost complete transformation of carboxaldehyde. The suspension was slowly added to a solution of KOH 90% (24.5 g, 0.3937 moles) in water (47 ml), followed by maintaining at 45-50° C. After 1 hour at 45° C., TLC analysis revealed complete hydrolysis, and a thick suspension was obtained. At this point toluene (120 ml) and water (180 ml) were added, and the suspension was cooled to 1-5° C. Then, 75% $H_3PO_4$ (about 50 g) was added drop-wise to obtain a pH in range of 5.4-5.8. During acidification $CO_2$ evolves and almost complete solid dissolution is observed. After the phases are separated, the organic phase was washed with water (200 ml) and then with sat NaCl, (100 ml). After solvent elimination under vacuum, a residual oil (47 g) of the title compound was obtained. (GC purity 91%.)

Example 19

2(2.3-Dihydrobenzofura-5-y)acetaldehyde, bisulfitic complex

In a four necked round bottomed flask equipped with thermometer, and mechanical stirrer, was loaded 2,3-Dihydrobenzofura-5-yl, acetaldehyde, of example 18 (47 g, 0.29 moles) and toluene (500 ml) to obtain a solution. Then, water (100 ml) and $Na_2S_2O_5$ (58.6 g) were added. The bisulfitic adduct precipitated and after 3 hours at room temperature it was filtered and washed twice with toluene (50 ml each). (Wet product: 95 g).

Example 20

2(2,3-Dihydrobenzofura-5-y)ethanol

The obtained wet bisulfitic adduct of example 19 was suspended in water (150 ml), and the pH was adjusted to 10-10.2 with NaOH 30%. $Na_2CO_3$ 10% (50 ml) and toluene (100 ml) were added and, after cooling to 5-10° C., a solution of $NaBH_4$ (5.8 g, 0.1526 moles)) in water (40 ml) was added drop-wise over about 45-60 minutes, while maintaining the pH at 9.8-10.2. The temperature was raised to 15-20° C. and after 1 hour the phases were separated. The aqueous phase was extracted with toluene (25 ml), and the combined organic phases were washed with water (50 ml). The solvent was eliminated under vacuum distillation, and the obtained oil solidified to give the title compound (26 g).

Example 21

Synthesis of (S)-2-{1-[2-(benzofuran-5-yl)ethyl]-3-pyrrolidinyl}-2,2-diphenylacetamide S-DIPAMP tartrate (12 g); BF-EtCl (5.6 g) $K_2CO_3$ (12 g) and Water 37.5 ml were heated at reflux for 5 hrs. After cooling to 85-90° C. n-butanol (60 ml) was added. After phases separation and washings (2×30 ml water) the organic phase was anhydrified by distillation and treated with $Ac_2O$ (0.65 ml) for three hrs. 48% HBr was added slowly and DRF-Ox-HBr crystallized. After 2 hrs at 15° C. the solid was filtered and washed with Butanol (3×5 ml). Wet solid was dried under vacuum at 50-55° C. for 15 hrs. (Dry weight 8.8 g).

Example 22

Synthesis of (S)-2-{1-[2-(2,3-dihydrobenzofuran-5-yl)ethyl]-3-pyrrolidinyl}-2,2-diphenylacetamide (DRF.HBr)

Pd/C 10% (0.8 g) was added to a solution of S)-2-{1-[2-(benzofuran-5-yl)ethyl]-3-pyrrolidinyl}-2,2-diphenylacetamide (8 g) in acetic acid (160 ml). The mixture was hydrogenated at 45-50° C. and at atmospheric pressure for about 6-7 hrs. Catalyst was filtered off and solution was concentrated under vacuum obtaining an oily residue. n-Butanol (40 ml) was added and stirred to obtain a solution. 48% HBr (3.5 g) was added and a mixture n-Butanol/water was eliminated by distillation to reduce water content to less then 1%. Darifenacin .HBr crystallizes and after 2 hrs at 15-20° C. was filtered and washed with n-Butanol (3×5 ml). After drying at 55-60° C. under vacuum 8.1 g of Darifenacin hydrobromide were obtained. (Yield 85%).

Example 23

Preparation of Darifenacin hydrobromide

Water (ml 203) Potassium carbonate (g 65) and DBF-EtCl (g 29.7) were heated to 60-65° C. To the mixture (S)-DIPAMP Tartrate (g 65) was added and the heterogeneous mixture was heated to reflux (101-102° C.) for 5 hrs. After cooling to 85-90° C. n-Butanol (ml 325) was added and after stirring phases were separated.

The organic phase was washed twice with water ml 160 (each) and then water was removed from organic phase by vacuum distillation. n-Butanol (ml 160) and Acetic anhydride (ml 3.25) were added and the solution was stirred at 20-30° C. for 1 hr. 48% HBr (g 25.5) was dropped, water was removed by vacuum distillation and DRF-HBr crystallized. Initial volume was restored by addition of n-BuOH. Suspension was stirred at 15-20° C. for 2 hrs, than product was recovered by filtration. The cake was washed with n-Butanol (3×30 ml) and wet solid (85-90 g) was crystallized without drying.

Crude wet DRF-HBr (85 g), n-Butanol (455 ml) and charcoal (4.63 g) were warmed to reflux to obtain a solution. After half an hour charcoal was filtered off keeping mixture at near reflux. Clear solution at 100° C. was seeded with DBR.HBr and after 30 min at 100° C. the solution was cooled to 15-20° C. in 2 hrs. Suspension was stirred at 15-20° C. for 2 hrs and then product was recovered by filtration. Cake was washed with n-butanol (3×25 ml). Wet pure DRF-HBr was dried under vacuum at 50-55° C. for 10-12 hrs. Dry weight 59.2 g. Overall Yield 77.2%

Comparative Example 24

Example 8 from U.S. Pat. No. 5,096,890 (col. 12, ll. 1-52)

Preparation of 3-(S)-(−)-(1-carbamoyl-1,1-diphenyl-methyl)-1-[2-(2,3-dihydrobenzofuran-5-yl)ethyl] pyrrolidine (Alternative to Example 1(B))

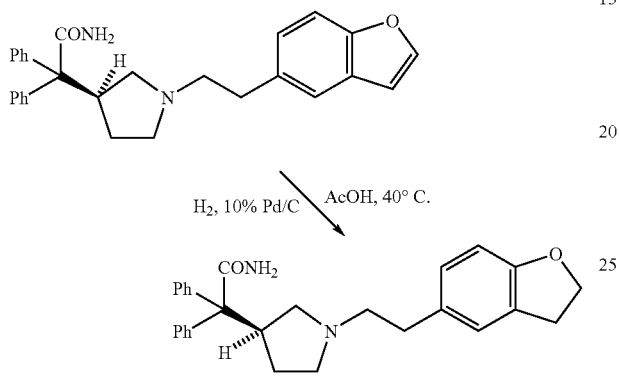

10% Palladium-on-carbon (10 mg) was added to a solution of 3-(S)-(−)-(1-carbamoyl-1,1-diphenylmethyl)-1-[2-(benzofuran-5-yl)ethyl]pyrrolidine (0.1 g—see Example 7) in acetic acid (2 ml) and the mixture was hydrogenated at 40° C. and atmospheric pressure for 6 hours. The catalyst was filtered off and washed with water (20 ml). The combined filtrate and washings were transferred to a separating funnel, dichloromethane (20 ml) was added, and the mixture was basified by the addition of 10% aqueous sodium hydroxide. The layers were separated and the aqueous layer was further extracted with dichloromethane (3×30 ml). The combined dichloromethane extracts were dried (MgSO$_4$) and concentrated in vacuo to give a colourless solid which was purified by column chromatography on silica eluting with dichloromethane containing methanol (4%). The product-containing fractions were combined and concentrated in vacuo to give the title compound as a colourless glass, yield 0.048 g, which was characterised spectroscopically to be identical to the product of Example 1(B).

$^1$H-N.M.R. (CDCl$_3$), δ=7.50-7.20 (m, 11H); 7.00 (s, 1H); 6.90 (d, 1H); 6.70 (d, 1H); 5.45-5.30 (brs, 1H); 4.60-4.50 (t, 2H); 3.60-3.45 (m, 1H); 3.25-3.15 (t, 2H); 3:05-2.50 (m, 8H); 2.10-1.95 (m, 2H) ppm.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments as falling within the true spirit and scope of the present invention.

We claim:

1. (S)-darifenamine of formula VII

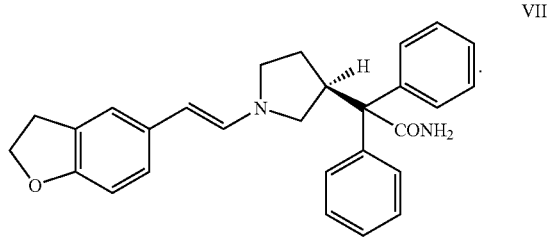

* * * * *